US008798722B2

(12) United States Patent
Rylander et al.

(10) Patent No.: US 8,798,722 B2
(45) Date of Patent: Aug. 5, 2014

(54) FIBER ARRAY FOR OPTICAL IMAGING AND THERAPEUTICS

(75) Inventors: Christopher Rylander, Blacksburg, VA (US); Thomas A. Campbell, Christiensburg, VA (US); Ge Wang, Blacksburg, VA (US); Yong Xu, Blacksburg, VA (US); Mehmet Alpaslan Kosoglu, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 37 days.

(21) Appl. No.: 13/203,800

(22) PCT Filed: Mar. 1, 2010

(86) PCT No.: PCT/US2010/025809
§ 371 (c)(1),
(2), (4) Date: Aug. 29, 2011

(87) PCT Pub. No.: WO2010/099548
PCT Pub. Date: Sep. 2, 2010

(65) Prior Publication Data
US 2011/0313298 A1 Dec. 22, 2011

Related U.S. Application Data

(60) Provisional application No. 61/156,273, filed on Feb. 27, 2009.

(51) Int. Cl.
*A61B 5/00* (2006.01)
(52) U.S. Cl.
USPC ............................................ 600/478; 600/476
(58) Field of Classification Search
CPC ..... A61B 5/0066; A61B 5/6848; A61B 5/685
USPC ................................................ 600/473–478
See application file for complete search history.

(56) References Cited

U.S. PATENT DOCUMENTS 5,483,958 A * 1/1996 Merberg et al. ............... 600/321
6,148,223 A * 11/2000 Davis et al. ................... 600/407
(Continued)

FOREIGN PATENT DOCUMENTS

| WO | 0250584 A2 | 6/2002 |
| WO | 2010099548 A | 9/2010 |
| WO | 2012154284 A | 11/2012 |

OTHER PUBLICATIONS

International Application No. PCT/US10/25809, International Preliminary Report on Patentability, Aug. 30, 2011.

(Continued)

*Primary Examiner* — Peter Luong
(74) *Attorney, Agent, or Firm* — New River Valley IP Law, PC; Michele L. Mayberry

(57) ABSTRACT

The present invention relates to the field of optical imaging and therapeutics. More particularly, embodiments of the present invention provide minimally-invasive Fiberoptic Microneedle Devices (FMDs) for light-based therapeutics, which physically penetrate tissue and deliver light directly into the target area below the skin surface (FIG. 1). A preferred embodiment of the invention is a fiberoptic microneedle device comprising: (a) one or more silica-based needles capable of guiding light and comprising a length of about 0.5-6 mm, a base having an outer diameter in the range of about 100-150 micron, and a tip having an outer diameter in the range of about 5-20 micron; (b) a support member to which the needles are secured; (c) a ferrule comprising one or more holes for each of the needles, wherein the ferrule is operably configured to provide mechanical support to each needle at all or some portion of the length of the needle. Embodiments of the invention enable depth-selective and deep photothermal therapeutics and can be adapted for use with any laser-based treatment or diagnostic in which light is used to detect or treat targets under or on the skin surface.

23 Claims, 22 Drawing Sheets

Fiberoptic Microneedle Device (FMD) Demonstrating Insertion of Microneedles into Skin

(56) References Cited

U.S. PATENT DOCUMENTS

| | | |
|---|---|---|
| 6,355,054 B1 | 3/2002 | Neuberger |
| 6,564,087 B1 | 5/2003 | Pitris et al. |
| 7,027,478 B2 | 4/2006 | Ackley |
| 2003/0095582 A1 | 5/2003 | Ackley |
| 2005/0137531 A1 | 6/2005 | Prausnitz et al. |
| 2007/0032845 A1 | 2/2007 | Neuberger |
| 2007/0129713 A1 | 6/2007 | Weber |
| 2008/0140023 A1 | 6/2008 | McMillan |
| 2008/0269735 A1 | 10/2008 | Vila Echague et al. |
| 2013/0338627 A1 | 12/2013 | Rylander et al. |

OTHER PUBLICATIONS

International Application No. PCT/US10/25809, International Search Report, Oct. 14, 2010.

International Application No. PCT/US12/26968, International Search Report and Written Opinion, Nov. 26, 2012.

Anderson, R.R. and J.A. Parrish, "Selective Photothermolysis—Precise Microsurgery by Selective Absorption of Pulsed Radiation," Science, 1983, 220(4596): p. 524-527.

Anderson, R.R. and J.A. Parrish, "The Optics of Human-Skin," Journal of Investigative Dermatology, 1981, 77(1): p. 13-19.

Campos, V.B., et al., "Ruby laser hair removal: Evaluation of long-term efficacy and side effects. Lasers in Surgery and Medicine," 2000, 26(2): p. 177-185.

Davis, S.P., et al., "Insertion of microneedles into skin: measurement and prediction of insertion force and needle fracture force," Journal of Biomechanics, 2004, 37(8): p. 1155-1163.

Grossman, M.C., et al., "Damage to hair follicles by normal-mode ruby laser pulses," Journal of the American Academy of Dermatology, 1996, 35(6): p. 889-894.

Kaushik, S., et al., "Lack of pain associated with microfabricated microneedles," Anesthesia and Analgesia, 2001, 92 (2): p. 502-504.

Khumpuang, S., R. Maeda, and S. Sugiyama, "Design and fabrication of a coupled microneedle array and insertion guide array for safe penetration through skin," in Micromechatronics and Human Science, 2003, MHS 2003: Proceedings of 2003 International Symposium.

Li, Xingde, et al., Imaging needle for optical coherence tomography. Optics Letters. vol. 25, No. 20. Oct. 15, 2000.

Meyer, W., R. Schwarz, and K. Neurand, "The skin of domestic mammals as a model for the human skin, with special reference to the domestic pig," Curr Probl Dermatol, 1978, 7: p. 39-52.

Mumtaz, H., et al. 1996, "Laser Therapy for Breast Cancer: Mr Imaging and Histopathologic Correlation," Radiology, 200(3), pp. 651-658.

Nanni, C.A. and T.S. Alster, "Long-pulsed alexandrite laser-assisted hair removal at 5, 10, and 20 millisecond pulse durations," Lasers in Surgery and Medicine, 1999, 24(5): p. 332-337.

Prudhomme, M., et al., 1996, "Interstitial Diode Laser Hyperthermia in the Treatment of Subcutaneous Tumor," Lasers in Surgery and Medicine, 19(4), pp. 445-450.

Ramasubramanian, M.K., et al., "Mechanics of a mosquito bite with applications to microneedle design," Bioinspiration & Biomimetics, 2008, 3(4).

Ribeiro, J.M.C. and I.M.B. Francischetti, "Role of arthropod saliva in blood feeding: Sialome and post-sialome perspectives," Annual Review of Entomology, 2003, 48: pp. 73-88.

Robinson, D. S., et al., 1998, "Interstitial Laser Hyperthermia Model Development for Minimally Invasive Therapy of Breast Carcinoma," Journal of the American College of Surgeons, 186(3), pp. 284-292.

Roxhed, N., et al., 2007, "Penetration-Enhanced Ultrasharp Microneedles and Prediction on Skin Interaction for Efficient Transdermal Drug Delivery," Journal of Microelectromechanical Systems, 16(6), pp. 1429-1440.

Shergold, O. A., and Fleck, N. A., 2005, "Experimental Investigation into the Deep Penetration of Soft Solids by Sharp and Blunt Punches, with Application to the Piercing of Skin," Journal of Biomechanical Engineering-Transactions of the Asme, 127(5), pp. 838-848.

Utzinger, U., and Richards-Kortum, R. R., 2003, "Fiber Optic Probes for Biomedical Optical Spectroscopy," Journal of Biomedical Optics, 8(1), pp. 121-147.

Wang, C.M., Wang C. Y., Reddy, J. N., "Exact Solutions for Buckling of Structural Members," CRC Series in Computational Mechanics and Applied Analysis, 2004, pp. 35-40.

Yamaguchi, S., et al., "Efficient Nd:YAG laser end pumped by a high-power multistripe laser-diode bar with multiprism array coupling.," Applied Optics, 1996, 35(9): p. 1430-1435.

Co-Pending U.S. Appl. No. 14/002,058, filed Aug. 28, 2013, published as US 2013/0338627 on Dec. 19, 2013.

Co-Pending Application No. PCT/US12/26968, filed Feb. 28, 2012, Published as WO2012/154284 on Nov. 15, 2012.

Hood RL, Kosoglu MA, Parker M, Rylander CG, Effects of Microneedle Design Parameters on Hydraulic Resistance, J. Med Devices 2011; 5(3).

Hruby, G.W., et al., "Transurethral Bladder Cryoablation in the Porcine Model." Journal of Urology, 70 (2), 2007, pp. 391-395.

International Application No. PCT/US12/26968, International Preliminary Report on Patentability, Sep. 3, 2013, 8 pages.

Johnson, D.E., "Use of the Holmium: Yag (Ho: Yag) Laser for Treatment of Superficial Bladder Carcinoma." Lasers in Surgery and Medicine, 1994, 14(3): p. 213-218.

Kosoglu MA, Hood RL, Chen Y, Xu Y, Rylander MN, Rylander CG, "Fiber Optic Microneedles for Transdermal Light Delivery: Ex Vivo Porcine Skin Penetration Experiments," J. Biomech. Engr. 2010; 132(9):091014.

Kosoglu MA, Hood RL, Rossmeisl JH, Grant DC, Xu Y, Robertson JL, Rylander MN, Rylander CG, Fiberoptic Microneedles: Novel Optical Diffusers for Interstitial Delivery of Therapeutic Light, Laser Surg Med 2011; 43 (9):914-920.

Raghavan, R., et al., "Convection-enhanced delivery of therapeutics for brain disease, and its optimization." Neurosurg Focus, 2006. 20(4): p. E12.

Stupp, R., et al., "Radiotherapy plus concomitant and adjuvant temozolomide for glioblastoma." N Engl J Med, 2005. 352(10): p. 987-996.

Syed, H.A., et al., "Holmium: YAG Laser Treatment of Recurrent Superficial Bladder Carcinoma: Initial Clinical Experience." Journal of Endourology, 2001, 15(6): p. 625-627.

Vandergrift, W.A., et al., "Convection-enhanced delivery of immunotoxins and radioisotopes for treatment of malignant gliomas." Neurosurg Focus, 2006. 20(4): p. E13.

\* cited by examiner

Mosquito Fascicle Surrounded by Labium

Microneedle Penetration of Ex Vivo Porcine Skin at 3A) 0 mm; 3B) 0.5 mm; and 3C) 1 mm Insertion Distance.

Process for Manufacturing Fiberoptic Microneedles and Geometrical Parameters

Microneedle Guide and Supporting Device

Ferrule Array Device: (*left*) in contact with skin, and (*right*) compressed against skin, causing fiber tapers to penetrate skin Critical Buckling Force With and Without Support and the Range of Forces for Insertion into Skin Fiberoptic Microneedle Device (FMD) Schematic Illustration of: (left) device using compression between two rigid plates, and (right) device using layered elastomeric ferrule Laser Ablation of a Gelatin Phantom Using 1064 nm light (.1 W) for a) 0s and b) 3min.

Skin Anatomy, and Fluence Distribution with Surface Delivery Compared to Microneedle Delivery Fiberoptic Microneedle (length= 3mm, average diameter= 125 micron) Penetrating 2 mm Thick Pig Skin Sample.

Fiberoptic Microneedle Device (FMD) Demonstrating Insertion of Microneedles into Skin Figure 19: a) Overview of the FMD setup b) Close-up image of the device Polished Microneedle Delivering Light in Air a) Brightfield microscopy image of optical fiber before etching;
b) Brightfield microscopy image of optical fiber after etching; and
c) Color microscopy image of red laser delivery by the etched fiber.

a) Vacuum chamber, ferrule, and the fiberoptic microneedle; b) Fiberoptic microneedle penetrating 2 mm thick pig skin

FIBER ARRAY FOR OPTICAL IMAGING AND THERAPEUTICS

CROSS-REFERENCE TO RELATED APPLICATIONS

This application is a National Stage application under 35 USC 371 of Application No. PCT/US10/25809, filed Mar. 1, 2010, the disclosure of which is hereby incorporated by reference herein in its entirety. This application relies on the disclosure of and claims the benefit of the filing date of U.S. Provisional Application No. 61/156,273, filed Feb. 27, 2009, the disclosure of which is incorporated by reference herein in its entirety.

BACKGROUND OF THE INVENTION

1. Field of the Invention

The present invention relates to the field of optical imaging and therapeutics. More particularly, embodiments of the present invention provide minimally-invasive Fiberoptic Microneedle Devices (FMDs) for light-based therapeutics, which physically penetrate tissue and deliver light directly into the target area below the skin surface (FIG. 1). Embodiments of the invention enable depth-selective and deep photothermal therapeutics.

2. Description of the Related Art

A major limitation for bio-imaging, including optical imaging and therapeutics (such as hair removal or optical tomography techniques, such as OCT imaging), is the shallow penetration depth of light in turbid tissue such as skin. Due to both scattering and absorption of the laser's photons by inhomogeneous tissue structures within the epidermis and dermis such as cells, collagen fibers, and aqueous ground substance, it is difficult if not impossible to maintain a focused or collimated beam past 1 mm depth into tissue. In particular, due to photon scattering around water-encapsulated and water-containing cells, focused light penetration into subcutaneous tissue is prevented, rendering the maximum typical photonic penetration depth of only a few millimeters. Enhancing photonic delivery past this current barrier would enable more selective, deeper, light-based therapeutics and diagnostics.

Currently, light-based therapeutics including oncology treatments, dermatology treatments, cosmetic surgeries, and alternative medicine protocols are limited in the results achieved and/or are not desirable by patients due to the pain typically associated with current procedures for performing these treatments. More specifically, applications that could benefit from improved light-based therapeutics (in particular, increased light penetration in skin) include a broad range of therapeutics ranging from the treatment of deep skin cancers such as melanoma to cosmetic procedures such as laser hair removal, especially for darker-skinned patients. By reaching targets beneath the skin surface, such as blood vessels, hair follicles, subdermal fat, and tattoo particles, to name a few, laser-based therapies and cosmetic applications including skin tightening, wrinkle removal, body contouring (fat reshaping or removal), and cellulite reduction could be substantially improved.

For example, minimally invasive laser-based hyperthermia therapy of cancers under the skin, such as melanoma, is currently not feasible due to the shallow penetration of light past the tumor surface. Such therapeutics could be feasible, however, by delivering light several millimeters deep in the tumor. By directly delivering optical radiation in near proximity to target tissue by way of minimally invasive optical fiber needles, the optical dose can be more precise, reducing unwanted collateral tissue damage and associated pain, and faster wound healing (with less scarring and bleeding) can be achieved. Increasing the amount of light penetration could also lead to the detection (and treatment) of tumors located several millimeters beneath the skin's surface through the use of laser-based methods.

Previous research has demonstrated that the light penetration problem can be overcome by using optical fibers to mechanically penetrate skin tissue for the purposes of transmitting light into desired areas. See Prudhomme, M., et al., 1996, "Interstitial Diode Laser Hyperthermia in the Treatment of Subcutaneous Tumor," Lasers in Surgery and Medicine, 19(4), pp. 445-450, the disclosure of which is incorporated by reference herein in its entirety.

Additionally, it has been known to place a silica optical fiber inside a 3.05 mm thick metal cannula with a light diffusing cap made from quartz. Robinson, D. S., et al., 1998, "Interstitial Laser Hyperthermia Model Development for Minimally Invasive Therapy of Breast Carcinoma," Journal of the American College of Surgeons, 186(3), pp. 284-292, the disclosure of which is incorporated by reference herein in its entirety. This design was used to deliver 1064 nm Nd:YAG laser light several centimeters deep into breast tumors.

Vertical cavity surface emitting lasers (VCSELs) are also known. For example, U.S. Pat. No. 7,027,478, entitled "Microneedle Array Systems," the disclosure of which is incorporated by reference herein in its entirety, discloses a device comprising an array of hollow microneedles that are 250 microns in length and have an entrance hole that is 175-200 microns in diameter and an exit hole diameter of 125 microns. Within the hollow portion of the needle (the interior channel) an optical fiber is placed for transmission of light through the needle (which is made of metal and is prepared using photolithography or laser drilling, or is made of high-temperature plastic). Such needles are large and could cause unnecessary damage if inserted into skin. Further, the disclosure does not support extending the technology to smaller needles, and is silent on using additional support means for supporting and guiding the needles during insertion into skin, due to the needles themselves being made of a material (metal or plastic) and having a configuration (large) the combination of which provides sufficient strength to the needles themselves.

Other probe designs were developed for use in diagnostic methods such as optical coherence tomography and optical spectroscopy. See Li, X. D., et al., 2000, "Imaging Needle for Optical Coherence Tomography," Optics Letters, 25(20), pp. 1520-1522; and Utzinger, U., and Richards-Kortum, R. R., 2003, "Fiber Optic Probes for Biomedical Optical Spectroscopy," Journal of Biomedical Optics, 8(1), pp. 121-147, the disclosures of both of which are incorporated by reference herein in their entireties. The fiberoptic probes used in these studies, however, are on the order of 300 μm to several millimeters in diameter. See, e.g., Robinson 1998; Prudhomme 1996; Li 2000; and Mumtaz, H., et al. 1996, "Laser Therapy for Breast Cancer: Mr Imaging and Histopathologic Correlation," Radiology, 200(3), pp. 651-658, the disclosure of which is incorporated by reference herein in its entirety.

With respect to physically penetrating skin (e.g., by mechanical means), while reducing or eliminating pain typically encountered by patients undergoing these procedures, it would be desirable to follow a pain-free microneedle model provided in nature—the mosquito fascicle. A mosquito has evolved to penetrate the skin with a flexible biological needle that is extremely small and flexible, inserting it into the skin to draw a meal of blood. The subsequent irritation caused by a mosquito bite is due to the allergic reaction to the saliva that the mosquito secretes during the blood draw to prevent platelet aggregation, not due to the needle insertion itself. See, Ribeiro, J. M. C. and I. M. B. Francischetti, "Role of arthropod saliva in blood feeding: Sialome and post-sialome perspectives," Annual Review of Entomology, 2003, 48: pp. 73-88, the disclosure of which is incorporated by reference herein in its entirety.

Mosquito-performed blood extraction is done through the fascicle which is covered by an outer sheath called the labium. An SEM photograph of a fascicle tip protruding from the end of the partially retracted labium is shown in FIG. 2. See, Ramasubramanian, M. K., et al., "Mechanics of a mosquito bite with applications to microneedle design," Bioinspiration & Biomimetics, 2008, 3(4), the disclosure of which is incorporated by reference herein in its entirety. The dimensions of the mosquito fascicle are typically 1.8 mm long with a 40 µm outer diameter. The tip of the fascicle is very sharp, tapering from about 10 µm to less than 1 µm over the last 50 µm of the fascicle. The fascicle is a polymeric microneedle composed of a ductile material, chitin, with an elastic modulus between 10 and 200 GPa (Ramasubramanian 2008) (similar to the inventive silica microneedles). The critical buckling load for a typical fascicle alone is very low (~3 mN) and not sufficient to penetrate the skin (>10 mN required); however, the lateral support provided by the labium increases the critical buckling load by a factor of 5 and permits successful skin penetration.

Buckling is the most common mode of failure for slender objects forced along their axial direction. This is true for silica-fiber-based fiberoptic microneedles as well. Increasing the buckling force of light guiding needles having a length/diameter ratio of approximately 50 is a challenge. The critical buckling force of a straight cylindrical column with fixed ends can be approximated using Euler's equation. See, Wang, C. M., Wang C. Y., Reddy, J. N., "Exact Solutions for Buckling of Structural Members," CRC Series in Computational Mechanics and Applied Analysis, 2004, the disclosure of which is incorporated by reference herein in its entirety.

A microneedle 2 mm long can safely penetrate skin if its diameter is larger than about 150 µm, which is close to the size of a wood splinter or a standard optical fiber, which are both known to penetrate the skin and inflict some level of pain. As shown in FIG. 3, the critical buckling force of silica microneedles (E=73 GPa for silica) with 2 mm unsupported length is plotted vs. diameter, and, for comparison, the penetration force required for microneedle insertion into skin obtained from results by Davis et al. is also shown. See, Davis, S. P., et al., "Insertion of microneedles into skin: measurement and prediction of insertion force and needle fracture force," Journal of Biomechanics, 2004, 37(8): p. 1155-1163, the disclosure of which is incorporated by reference herein in its entirety.

In order to improve the feasibility of using much smaller, less invasive nano- and micro-needles in clinical applications, the critical buckling force of the needles must be improved. Enhancing photonic transmission depth without absorption and scattering to allow imaging and light-based therapeutics below the epidermis (top 100 µm) and dermis (1-2 mm thick below epidermis) would have important implications in basic research (individual cell imaging), tissue engineering, and tissue therapeutics.

What is needed, and what embodiments of the present invention provide, are thinner fiberoptic microneedles (140 µm or less in diameter) for substantially reducing the morbidity and associated pain caused by insertion of needles into living tissue.

SUMMARY OF THE INVENTION

To address some of the issues relating to light-based therapeutic procedures, embodiments of the present invention provide minimally invasive fiberoptic microneedles (e.g., probes) capable of physically (by way of mechanical means) penetrating tissue to deliver light directly to target areas below the skin surface.

Objects of embodiments of the present invention provide: 1) novel microneedle structures including but not limited to silica solid, hollow-core, and photonic crystal fibers; 2) methods and devices for mechanically (physically) inserting these microneedle fiber arrays into human tissue; and 3) novel biomedical applications involving light/fluid transport through these fibers and tissue for applications including: i) photo-therapy, ii) optical sensing or imaging for diagnostics, iii) fluid/drug delivery, iv) biochemical sensing/diagnostics; and v) multi-modal combinations of the aforementioned applications.

In embodiments of the invention, the fiberoptic microneedle device (FMD) bypasses the turbid skin barrier by insertion of extremely small light-delivering microneedles in proximity to the target tissue. The microneedles are mechanically stabilized to prevent buckling and are painlessly guided into a patient's skin using a novel guidance ferrule template and an elastomeric material. The FMD allows increased light penetration in skin and can substantially improve a variety of light-based therapeutic and diagnostic procedures.

Embodiments of the invention comprise a fiberoptic microneedle or an array of fiberoptic microneedles for light delivery using brightfield imaging in tissue representative phantoms. Embodiments also include a fiberoptic microneedle device (FMD) capable of penetrating skin using white light photographic imaging and thermal imaging during laser irradiation. Methods for using such fiberoptic needles and FMDs to treat a variety of conditions or diseases are also within the scope of the invention.

Fiberoptic microneedles and microneedle devices according to the present invention can comprise a support member for increasing the critical buckling force of the needle(s) to fortify the needles for insertion into skin. It has been found that if a microneedle is embedded inside an elastic medium such as a polymer, the medium will act like a series of springs that limit the lateral movement of the microneedle, increasing its critical buckling force, and enabling skin penetration similar to the mechanism used in mosquito bites.

Further, embodiments of the invention include light guiding microneedles manufactured from standard multimode silica fibers. An exemplary method for manufacturing such fiberoptic needles is by drawing silica fibers into a tapered (needle-like) shape by heating the fibers to their melting temperature and stretching them with a mechanical stage. Such a manufacturing process allows for needles with different geometries to be made, including needles having centimeter lengths and/or sub-micron tip diameters.

A range of various needle geometries have shown potential. For example, using white-light photographic imaging with a stereo microscope, FIG. 3 provides a sequence of photographic images demonstrating the feasibility of 1 mm needle penetration into ex vivo porcine skin. The needle in this example remained intact (buckling not observed) even after removal from the skin, in part due to the high taper angle of the needle. A penetration depth of up to 1 mm is sufficient to bypass the epidermal layer of the skin, which contains melanin, the matter responsible for much of the light absorption in light-based therapeutics.

Embodiments of the invention can also comprise additional mechanical support or strengthening of the needle, for providing a range of feasible microneedle variations for numerous applications. Toward this end, embodiments of devices of the invention can comprise an array of optically transparent fibers (either nano- or microscale in diameter), which are capable of being guided into a patient's skin using a guidance ferrule template and an elastomeric support material for increasing the buckling force of the needle(s).

DETAILED DESCRIPTION OF VARIOUS EMBODIMENTS OF THE INVENTION

Figure 1:
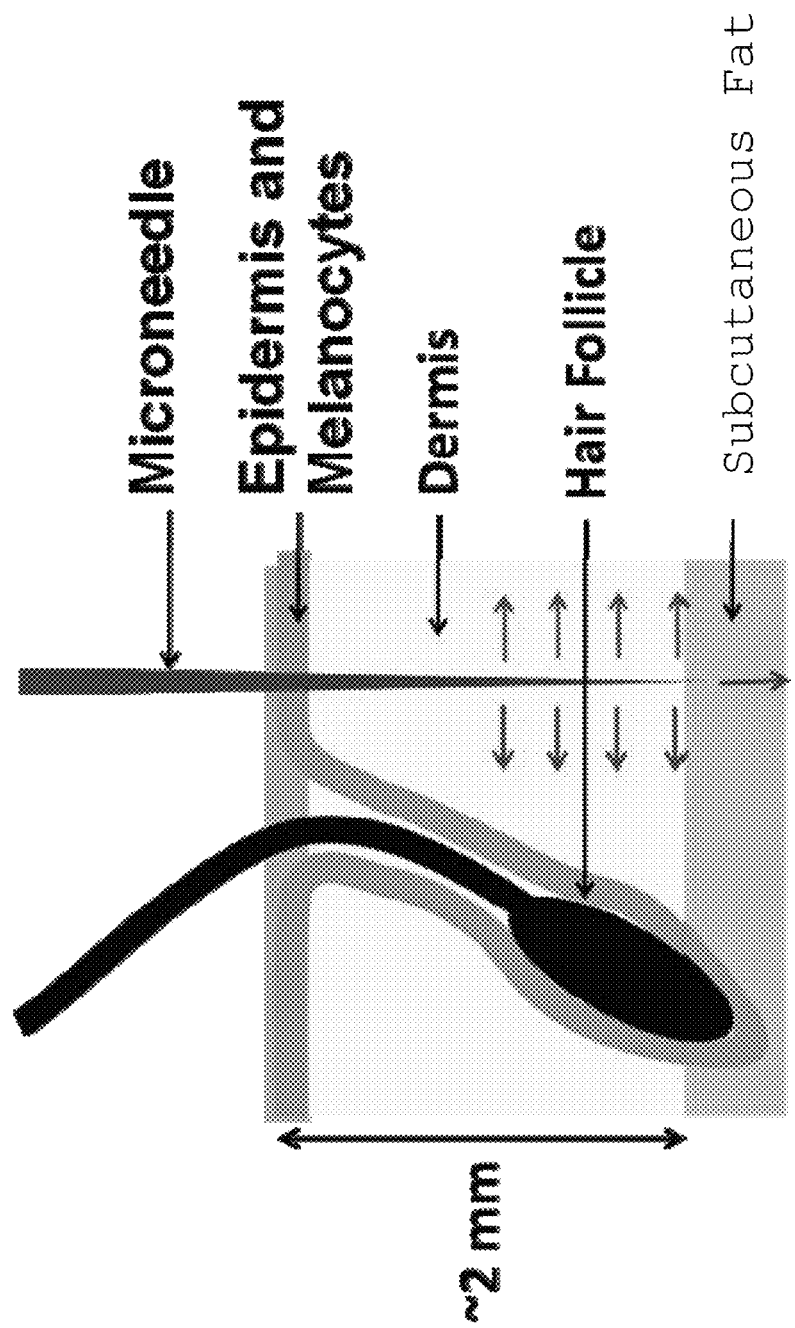
FIG. 1 is a schematic diagram showing a fiberoptic microneedle according to the invention inserted to a depth (approx. 2 mm) below the surface of the skin, to place the needle in a position for delivering light to a target (e.g., hair follicle) of a light-based therapy.

Reference will now be made in detail to various exemplary embodiments of the invention. The following detailed description is presented for the purpose of describing certain embodiments in detail and is, thus, not to be considered as limiting the invention to the embodiments described. Rather, the true scope of the invention is defined by the claims.

Embodiments of the invention provide (aspect 1) a non-metal needle comprising structure for transmitting light, which is capable of piercing human tissue, and has a maximum diameter in the range of about 100-300 micron. Also included are (aspect 2) needles of aspect 1 comprising a base having an outer diameter in the range of about 100-300 micron and a tip having an outer diameter in the range of about 5-50 micron. Further provided are (aspect 3), needles of aspect 2 comprising a base having an outer diameter in the range of about 100-200 micron and a tip having an outer diameter in the range of about 5-40 micron. Aspect 4 provides needles of aspect 3 comprising a base having an outer diameter in the range of about 100-150 micron and a tip having an outer diameter in the range of about 5-20 micron. Aspect 5 provides needles of aspect 4 comprising a base having an outer diameter in the range of about 100-125 micron and a tip having an outer diameter in the range of about 5-10 micron.

A non-metal material or "non-metal" as used in this disclosure refers to any material that is a poor conductor of heat and electricity. Non-metals in accordance with the present invention can also include materials having a thermal conductivity (at about 25° C.) of about 5 k (W/mK) or less, such as about 2-4 k, or such as about 1 k or less. Silica or silica-based materials or fibers, even though they may contain metals in their compositions are non-metals according to the invention. Ceramics, quartz, plastics, and polymers are also non-metals according to the invention, including many other materials having similar properties. In contrast, aluminum, copper, iron, alloys, brass, nickel, silver, gold, lead, molybdenum, zinc, magnesium, stainless steel, etc. for example are exemplary metals.

Aspect 6 provides needles of aspect 5 comprising a hollow core having an inner diameter in the range of about 1-8 micron. Aspect 7 provides the needle of any of aspects 1-6 having a length of about 0.5-6 mm. Aspect 8 provides the needle of any of aspects 1-7 having a length of about 1-3 mm. Aspect 9 provides the needle of any of aspects 6-8 comprising a hollow core having an inner diameter in the range of about 1-5 micron.

Aspect 10 provides the needle of any of aspects 1-9, wherein the light-transmitting material is silica. Aspect 11 provides the needle of any of aspects 1-10 comprising multi-mode silica fiber. Aspect 12 provides the needle of any of aspects 1-10 comprising single-mode silica fiber. Aspect 13 provides the needle of any of aspects 1-12 comprising a flat or non-tapered tip. Aspect 14 provides the needle of any of aspects 1-12 comprising a tapered tip end, wherein the needle has a first taper defined by an outer diameter that becomes increasingly smaller along a length of the needle toward the tip end and a second taper defined by an outer diameter that becomes increasingly smaller within 10-20% of the tip end based on overall needle length.

Aspect 15 provides the needle of any of aspects 1-14 comprising a light-blocking coating. Aspect 16 provides the needle of any of aspects 1-15, wherein the structure is formed from heating and stretching a silica-based fiber cylinder or rod, having a first average outer diameter along the length of the fiber, until a second outer diameter smaller than the first is obtained in a region of the fiber and breaking the fiber at a point in the second smaller diameter region. Aspect 17 provides the needle of aspect 16, wherein breaking of the fiber involves stopping the heating and stretching of the fiber, cooling the fiber, and mechanically breaking the fiber. Aspect 18 provides the needle of aspect 16, wherein breaking of the fiber involves direct laser heating at a point in the second smaller diameter region combined with stretching of the fiber at a rate sufficient to obtain a third outer diameter smaller than the second and sufficient to break the fiber at a point in the third smaller diameter region to form a tapered tip.

Also included in embodiments of the invention is (aspect 19) a fiberoptic microneedle device comprising: (a) one or more needles of any of aspects 1-18; (b) a support member to which the needles are secured; and (c) a ferrule comprising one or more holes for each of the needles, wherein the ferrule is operably configured to provide mechanical support to each needle at all or some portion of the length of the needle. Further included (aspect 20) is a fiberoptic microneedle device comprising: (a) one or more silica-based needles capable of guiding light and comprising a length of about 0.5-6 mm, a base having an outer diameter in the range of about 100-150 micron, and a tip having an outer diameter in the range of about 5-20 micron; (b) a support member to which the needles are secured; and (c) a ferrule comprising one or more holes for each of the needles, wherein the ferrule is operably configured to provide mechanical support to each needle at all or some portion of the length of the needle.

Aspect 21 provides the device of aspect 19 or 20 comprising an array of needles.

Aspect 22 provides the device of any of aspects 19-21, wherein the ferrule is flexible. Aspect 23 provides the device of any of aspects 19-21, wherein the ferrule is rigid. Further, aspect 24 provides the device of any of aspects 19-21, wherein the ferrule is a combination of flexible and rigid materials.

Embodiments of the invention include (aspect 25) the device of any of aspects 19-24 comprising an electrical, mechanical, pneumatic, or hydraulic actuation source for inserting the needles into the ferrule, moving the needles within the ferrule, or causing protrusion of a portion of the needles from the ferrule. Further, aspect 26 provides the device of any of aspect 19-22 or 24-25 comprising means for compressing the flexible ferrule or flexible portion of the ferrule against a surface to cause the needles to protrude from the ferrule into the surface. In embodiments (aspect 27) there is the device of aspect 26 which can be used with human skin.

Aspect 28 provides the needle of any of aspects 1-18 or the device of any of aspects 19-27 comprising a light source operably connected with the needles to transmit light through the needles. Aspect 29 provides the needle or device of aspect 28, wherein the light source is a laser. Aspect 30 provides the device of any of aspects 19-29 comprising a control system with feedback capabilities to monitor and control power and duration of light delivery from the needles; or monitor and control pressure, volume, and rate of flow of fluids or particles through the needles; or monitor and control depth of protrusion of the needles from the ferrule.

Aspect 31 is the device of any of aspects 19-30 comprising means for applying positive or negative vacuum pressure for temporarily securing the ferrule to a surface and stabilizing the device for insertion of the needles into the surface from and through the ferrule.

Also included in embodiments of the invention is a method (aspect 32) of performing photothermal, photochemical, or photomechanical therapy in tissue comprising delivering light on a tissue surface, in a tissue surface, or below a tissue surface using any needle of aspects 1-18 or any device of aspects 19-31. Aspect 33 provides a method of detecting disease in tissue comprising delivering light on a tissue surface, in a tissue surface, or below a tissue surface using any needle of aspects 1-18 or any device of aspects 19-31 to collect data about the tissue. Aspect 34 provides the method of aspect 32 or 33 comprising delivering light below a surface. Aspect 35 provides the method of aspect 34, wherein the surface is a human skin surface.

These embodiments are described in greater detail below. For convenience, Table 1 below provides a list of terms used in this disclosure and their corresponding definitions.

TABLE 1

List of Terms

| | |
|---|---|
| $\alpha_T$: | Taper angle of flat microneedles |
| $\alpha_{T1}$: | First taper angle of sharp microneedles |
| $\alpha_{T2}$: | Second taper angle of sharp microneedles |
| $\lambda$: | Wavelength of light |
| $CO_2$: | Carbon dioxide |
| CCD: | Charge-coupled device |
| $d_{AVG}$: | Average diameter of a microneedle |
| $d_{AVG, FLAT}$: | Average diameter of a flat microneedle |
| $d_{AVG, SHARP}$: | Average diameter of a sharp microneedle |
| $d_{BASE}$: | Base diameter of a microneedle |
| $d_{INF}$: | Diameter at inflection point for sharp microneedles |
| $d_{TIP}$: | Tip diameter of a microneedle |
| E: | Elastic modulus of silica |
| F1-8: | Flat microneedles |
| L: | Unsupported length |
| $L_{TIP}$: | Tip length, length of the second taper |
| $F_{CR}$: | Critical buckling force of a microneedle |
| $F_{INS}$: | Skin insertion force |
| Nd:YAG: | Neodymium-doped Yttrium Aluminium Garnet |
| S1-12: | Sharp microneedles |

Needles according to embodiments of the invention, or used with device embodiments of the invention, can comprise any length, diameter, tapering characteristics, material, wall thickness, etc. desirable or needed for a particular application. For example, the microneedles of the invention can range from 1 mm to 5 mm in length. A preferred length of microneedle (selected to satisfy the light penetration depth needed for skin carcinoma applications) is a 3 mm long microneedle. Such microneedles can be used to physically penetrate skin and deliver light into subdermal locations.

Any length needle can be used in accordance with the present invention, including needles that are 0.5 mm, 1 mm, 1.5 mm, 2 mm, 2.5 mm, 3 mm, 3.5 mm, 4 mm, 4.5 mm, 5 mm, 5.5 mm, 6 mm, and so on in overall length. As used herein these lengths can refer to a measurement from the base to the tip of the needle, or can refer to the length of the portion of the needle intended to be inserted into skin.

Likewise, any diameter needle can also be used in accordance with the present invention, including needles that are 300 microns or less in diameter at any point on the needle. Preferred needle embodiments have a base diameter ranging from about 50 microns to about 500 microns and any diameter in that range. More specifically, preferred needle embodiments of the invention have a base diameter of about 100 microns to 200 microns, such as from about 140 microns to 175 microns, and such as from about 150-170 microns. Tip diameters of the needles of the invention can range from about 1 micron to 50 micron, such as from about 2-20 micron, such as from about 5-15 micron, or from about 3-12 micron, or any diameter in that range. If the needle has a hollow core (or liquid-filled core), then these diameter ranges are also applicable to the inside diameter of the core.

Preferred microneedles according to the invention include needles having a length ranging from about 500 to 1000 μm and a tip diameter ranging from about 5 to 10 and longer microneedles (about 2 to 4 mm) with smaller tip diameters (about 2-8 μm). Specific needle embodiments of the invention comprise fiberoptic microneedles with 125 μm root diameter and 2-8 μm tip diameter.

The needles can be solid throughout or comprise a hollow core. When referring to diameters in this disclosure, it is typically intended to refer to outer diameters of the needles, whether measured at the base or tip of the needle. In some cases a diameter mentioned may refer to the inner diameter of the hollow core of the needle.

The microneedles of the invention also comprise a range of acceptable aspect ratios. As used in this disclosure, an aspect ratio refers to the unsupported length of the needle divided by the average cross-sectional diameter of the needle. Preferred aspect ratios of microneedles, e.g., fiberoptic microneedles, of the invention range from about 21 to 85. Using these high aspect ratio microneedles to penetrate skin is a challenge due to possible failure by buckling under the skin's resistance. However, earlier studies have found that the skin insertion force ($F_{INS}$), the force which the microneedle is subjected to during insertion into the skin, varies linearly with the cross-sectional area of the tip. See, Davis, S. P., et al., 2004 "Insertion of Microneedles into Skin: Measurement and Prediction of Insertion Force and Needle Fracture Force," Journal of Biomechanics, 37(8), pp. 1155-1163, the disclosure of which is incorporated by reference herein in its entirety.

Figure 3:
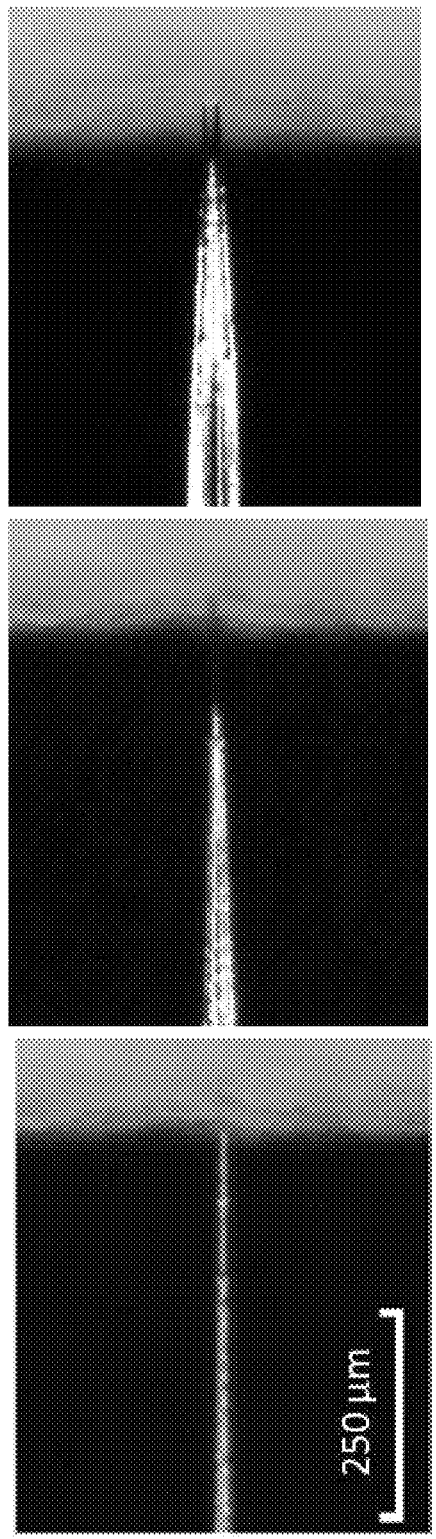
FIGS. 3A-C are a series of photographic images of a microneedle according to the invention that is inserted into skin at 0 mm, 0.5 mm, and 1 mm depths.

Microneedles were tested for their ability to penetrate mediums with different hardness. Needle penetration into skin was performed with porcine skin obtained from a local butchery. The microneedle used was able to penetrate the skin up to a 1 mm depth without breaking, which is a sufficient depth to bypass the epidermal layer of the skin, which scatters the most light. FIGS. 3A-C show photographic images of needle penetration into skin at 0 mm, 0.5 mm, and 1 mm, respectively.

Figure 4:
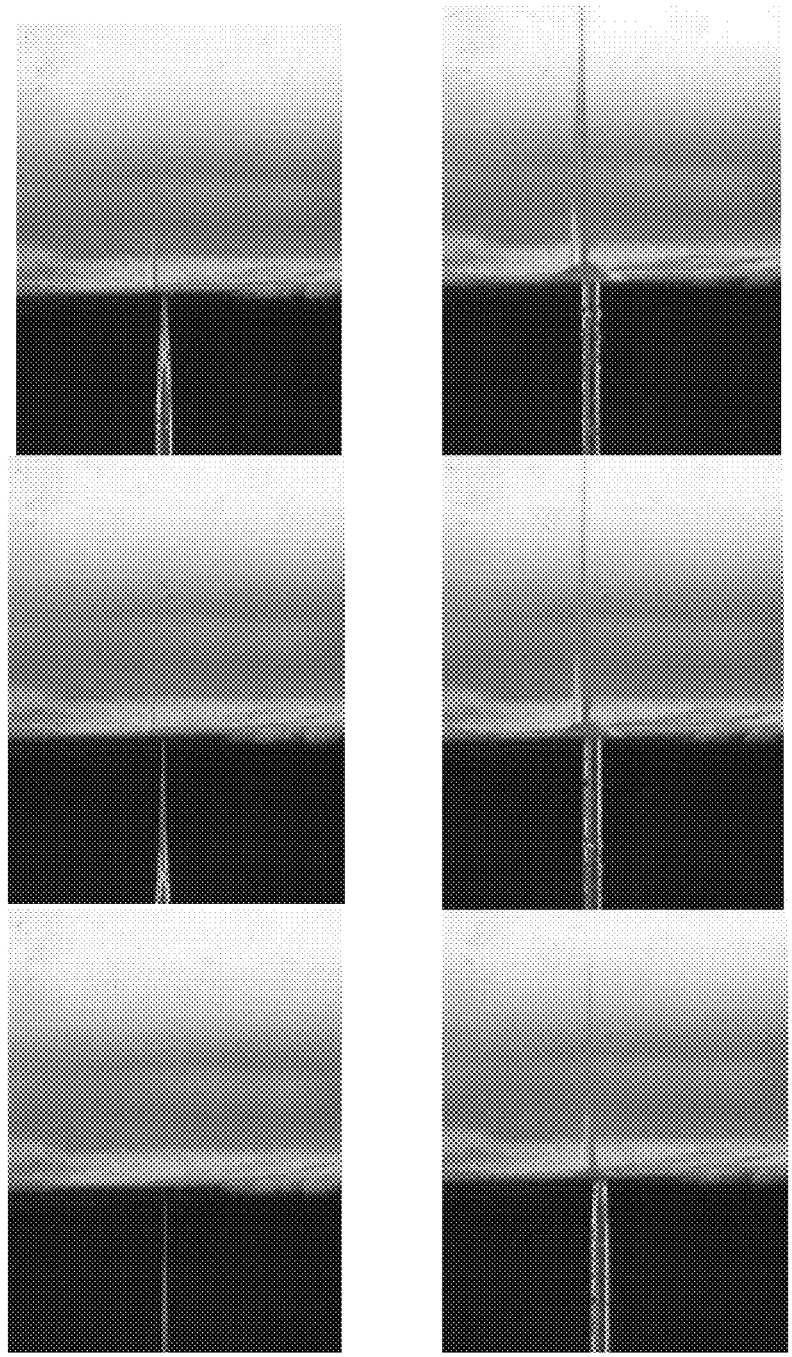
FIG. 4 provides a series of photographic images of a microneedle according to the invention inserted into skin at various intervals.

Additionally, a microneedle was placed on a micrometer translational stage, and it was manually inserted into a slice of store bought flavorless gelatin. FIG. 4 shows insertion of the microneedle into the medium at snapshots taken with 500 μm intervals. The needle was inserted into 2.5 mm depth without bending or any kind of skewing and remained intact even after withdrawal from the gelatin, which demonstrates that these light guiding microneedles are capable of penetrating into soft material.

Modifying the tip of the optical fiber to resemble a sharp needle would reduce the skin insertion force $F_{INS}$ while the critical buckling force ($F_{CR}$) would remain roughly the same. Through this method, skin penetration performance of hollow silicon microneedles has been improved by incorporating ultra-sharp tips with diameters of less than 1 μm. See, Roxhed, N., et al., 2007, "Penetration-Enhanced Ultrasharp Microneedles and Prediction on Skin Interaction for Efficient Transdermal Drug Delivery," Journal of Microelectromechanical Systems, 16(6), pp. 1429-1440, the disclosure of which is incorporated by reference herein in its entirety. In addition to decreasing $F_{INS}$, a sharp tip also modifies the forcing conditions on a microneedle during insertion.

In a recent study, a comparison of the penetration of ex vivo human skin by flat versus sharp-tipped punches was presented. See, Shergold, O. A., and Fleck, N. A., 2005, "Experimental Investigation into the Deep Penetration of Soft Solids by Sharp and Blunt Punches, with Application to the Piercing of Skin," Journal of Biomechanical Engineering-Transactions of the Asme, 127(5), pp. 838-848, the disclosure of which is incorporated by reference herein in its entirety. The flat punches were made from 300 and 500 μm thick stainless steel wires while 300 and 600 μm thick hypodermic needles were used as sharp punches. The results showed that penetration by sharp punches was accompanied by a growing mode I planar crack which caused a steady increase in the force. In contrast, the resistive force on the flat punches showed a rapid increase followed by an instant drop as the punch penetrated through the different skin layers due to the formation of a mode II ring crack. Considering the lower $F_{INS}$ and steadier force increase on sharp microneedles, the researchers hypothesized that sharp tips would make thinner, less invasive microneedles mechanically practical for penetrating skin.

Needle geometry can be varied to achieve particular desired effects and/or results. For example, the leakage length of fiberoptic microneedles (the axial length of the microneedle, along which the laser light leaks out of the microneedle and into the surrounding medium) can vary according to the taper length of the needle.

Figure 5:
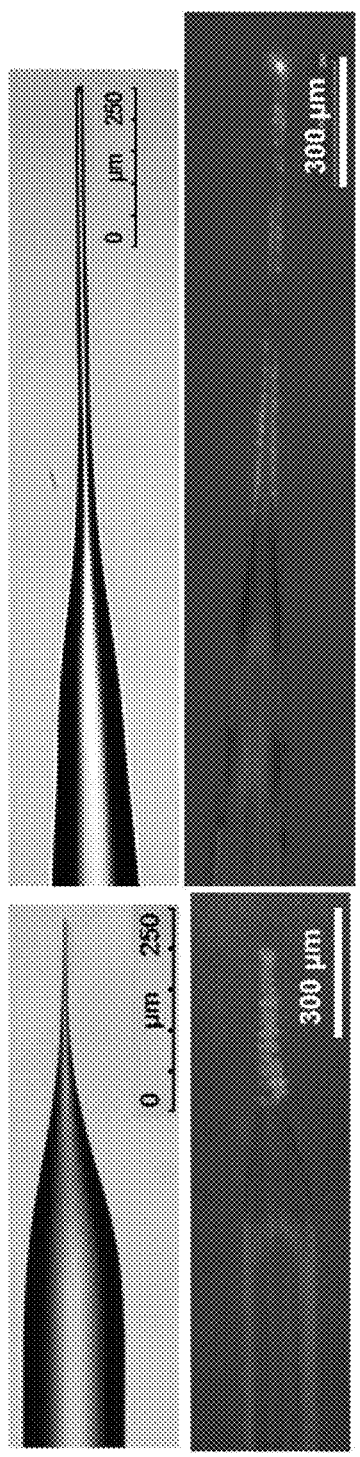
FIG. 5 provides brightfield microscopy images of two microneedles according to the invention having different taper lengths and color microscopy images of those needles delivering red laser light in air, demonstrating different leakage lengths for the needles.

The leakage length of several fiberoptic microneedles in air was measured in order to evaluate the importance of the microneedle geometry. In particular, various fiberoptic microneedles with differing taper lengths were used to deliver red laser light in air (FIG. 5). More particularly, FIG. 5 provides brightfield microscopy images of two microneedles according to the invention having different taper lengths and color microscopy images of those needles delivering red laser light in air. As shown, different needle geometries can provide different leakage lengths for the needles.

Table 2 lists values for taper and leakage lengths of various microneedles according to embodiments of the invention:

TABLE 2

Taper Lengths and Leakage Lengths for Various Microneedles

| Microneedle | Taper Length [μm] | Leakage Length [μm] |
|---|---|---|
| 1 | 380 | 177 |
| 2 | 1550 | 950 |
| 3 | 460 | 204 |
| 4 | 410 | 319 |
| 5 | 387 | 227 |
| 6 | 431 | 224 |
| 7 | 457 | 154 |
| 8 | 396 | 193 |
| 9 | 929 | 490 |
| 10 | 398 | 190 |

Figure 20:
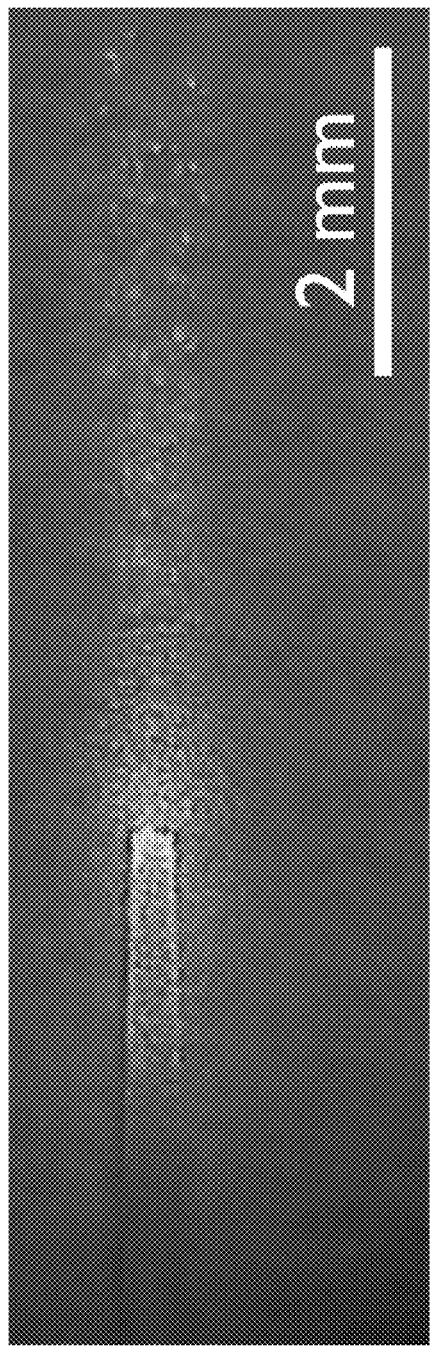
FIG. 20 is a photographic image of a light leaking microneedle.
Figure 21:
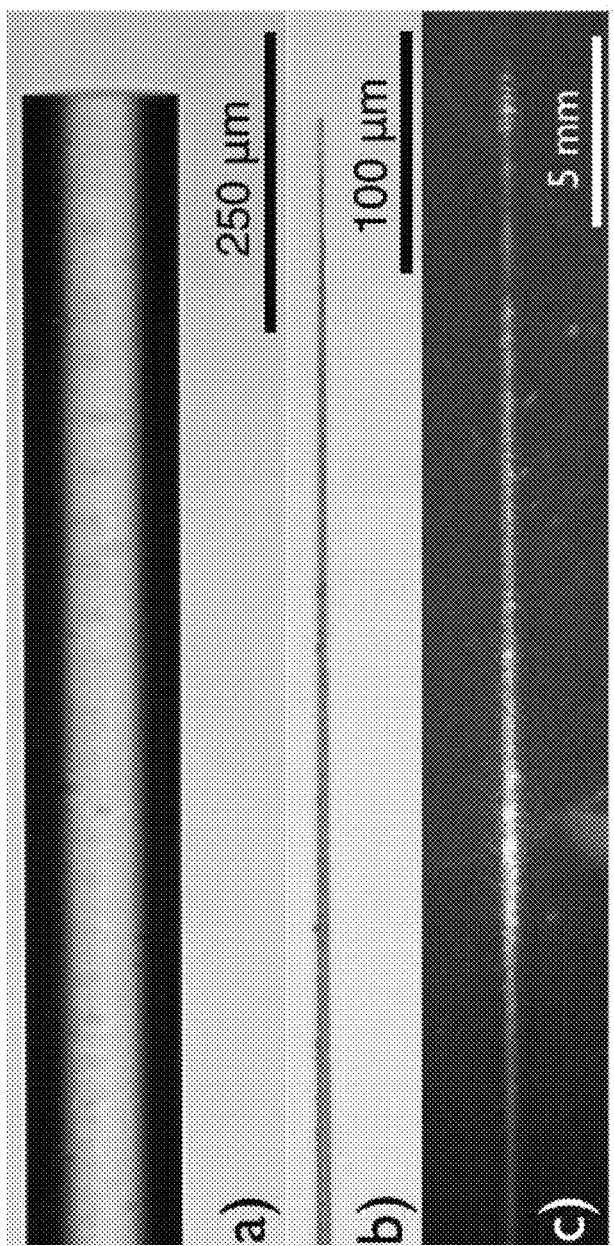
FIGS. 21A, B, and C are brightfield microscopy images showing the control of microneedle leakage length by removing the fiber cladding by HF etching.

Leakage length of fiberoptic microneedles varied according to their taper length. Longer tapers resulted in longer leakage lengths. Leakage length can be controlled by removing the fiber cladding by polishing. Fibers with larger core/cladding ratio and larger taper angles produce a longer leakage length. Leakage area of light can be controlled by changing the geometry of the fiberoptic microneedle. For example, a longer leakage length can be useful for delivering laser light along the shaft of a hair follicle while shorter leakage length limits the loss of light and provides deeper light penetration. Said another way, for certain therapeutic applications such as fat removal, a shorter leakage length causing a more forward-focused beam from the needle may be desirable, however, for hair removal applications, a more uniformly diffuse optical delivery to heat the vertical sides of the hair follicles is preferred and therefore longer leakage length needles may be desirable. Controlling the leakage length by removing the fiber cladding by polishing. As shown in FIG. 20, light leaking microneedles were manufactured by polishing the sides of a multimode optical fiber and removing the cladding. As shown in FIGS. 21A, B, and C, leakage length can be controlled by removing the fiber cladding by HF etching. In particular, a light leaking microneedle was manufactured by dipping a multimode optical fiber into a %48-50 HF solution for about an hour.

Any optical fiber can be used to make needle embodiments of the invention. It is not critical that the core or cladding material be of any particular material or configuration. For example, the core and cladding typically comprise materials with different refractive index characteristics to trap all or most of the light within the area bounded by the cladding and to ensure transmission of light through the core of the needle. Depending on the cladding material and/or whether the needle is coated with a light blocking material, some light may escape resulting in leakage horizontally through the needle instead of mostly vertically through the tip of the needle. In some applications horizontal leakage may be desired.

Light guiding microneedles were manufactured from optical fibers with 8 μm diameter silica core and 125 μm diameter silica cladding. These optical fibers were drawn down into a tapered (needle-like) shape by simultaneously heating the fiber to its melting temperature and stretching it with a mechanical stage. Heating of the optical fiber was done by two different methods, thereby producing microneedles with different geometries.

Figure 6:
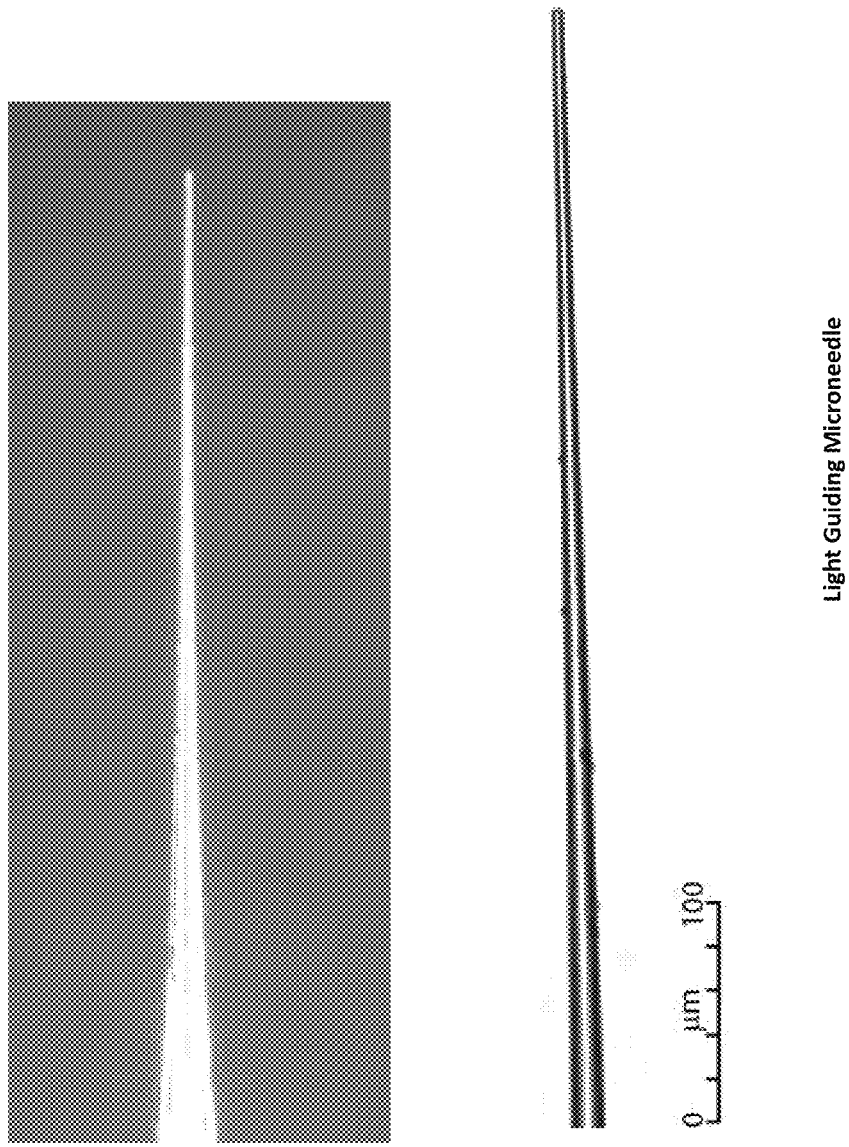
FIG. 6 shows photographic images of an embodiment of the inventive light guiding microneedles according to the invention.

Some microneedles were manufactured by heating the fiber by focusing the beam of a $CO_2$ laser on the fiber. As shown in FIG. 6, this method produced microneedles with lengths ranging from 500 to 1000 μm and with tip diameters of 5 to 10 μm. Longer microneedles (2 to 4 mm) with smaller tip diameters (2-8 μm) were obtained by placing half of a sapphire tube underneath the fiber and heating the tube with a propane-oxygen torch. The heat radiating from the tube softened the fiber slowly and made it possible to manufacture longer microneedles with smaller taper angles and smaller tip diameters.

Fiberoptic microneedles can be prepared from any material capable of transmitting light, with silica-based optical fibers being a preferred starting material. Light-guiding fiberoptic microneedles were manufactured from two kinds of commercially available, silica based, step-index optical fibers. The optical fibers were drawn into thinner fibers by simultaneously heating them to the melting temperature of silica (1650±75° C.) and stretching them with two mechanical stages (0.2-0.36 mm/sec drawing speed). Heating was provided by a heat-radiating sapphire tube, which was carefully placed around the fiber without any contact. The dimensions of the sapphire tube were 4 mm inner diameter, 6 mm outer diameter, and 8 mm length. A propane-oxygen torch was used to heat the sapphire tube. At this point in the process (Step I), the optical fiber had a thinner section toward the middle of the fiber, whereby the overall shape of the fiber resembled an hourglass shape. Depending on the duration of the tapering process, this thinner section varied between 6-8 mm in length. If the stretching and heating of the fiber was continued until the fiber broke apart at its thinnest cross-section, then two microneedles were produced with flat tips (referred to as flat microneedles).

To obtain lower $F_{INS}$ and steadier increase in the peak force, microneedles with sharp tips were manufactured. In order to produce microneedles with sharper tips, the heating and stretching of the fiber was halted before breaking the fiber. An additional step was then performed (Step II), a $CO_2$ laser ($\lambda$=10 μm) was focused onto the center of the narrow section of the fiber before continuing to stretch the optical fiber at a velocity of 0.05-0.1 mm/sec. Such rapid and focused heating produced a second taper, resulting in a sharper tip ($d_{TIP} \leq 8$ μm). The sapphire rod heated the optical fibers over a length of 8 mm while the $CO_2$ laser had a spot size of 400 μm in diameter.

Figure 7:
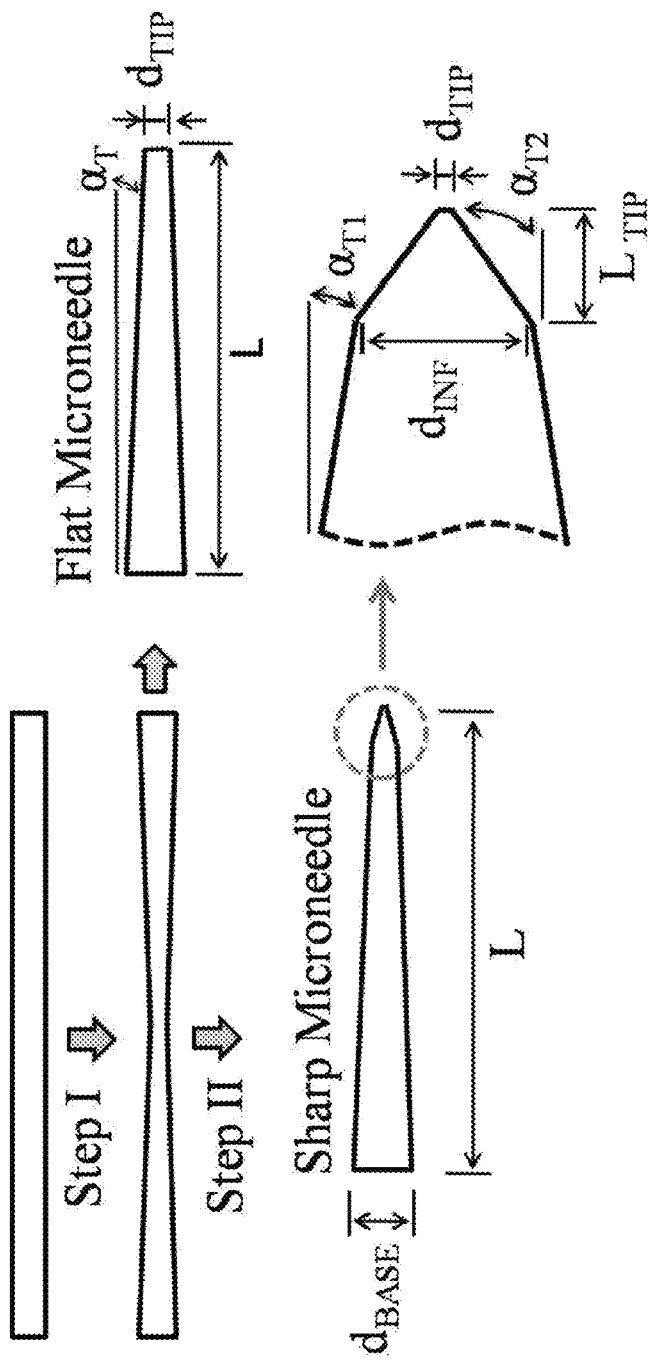
FIG. 7 is a schematic diagram of a manufacturing process for microneedles according to exemplary embodiments of the invention.

FIG. 7 shows a schematic of a manufacturing process for fiberoptic microneedles according to the invention and geometric parameters of both kinds of microneedles, i.e., flat-tip and sharp-tip needles. As shown, the fiber optic material is heated and stretched (Step I), which results in an overall hourglass shape in the material. For a flat tip, the hourglass shaped material is caused to break forming two flat-tip microneedles. For a sharp tip (Step II), the material is stretched and heated and focused heat is applied at a point in the material where it is desired to have a tip, typically at a mid point of the material during stretching. The heat can be provided by a $CO_2$ laser ($\lambda$=10 μm) and is applied with continued stretching of the material at a desired rate to cause the optical fiber to break while forming a second taper at the tip of the microneedle, which is referred to as a sharp tip due to the additional taper.

Figure 8:
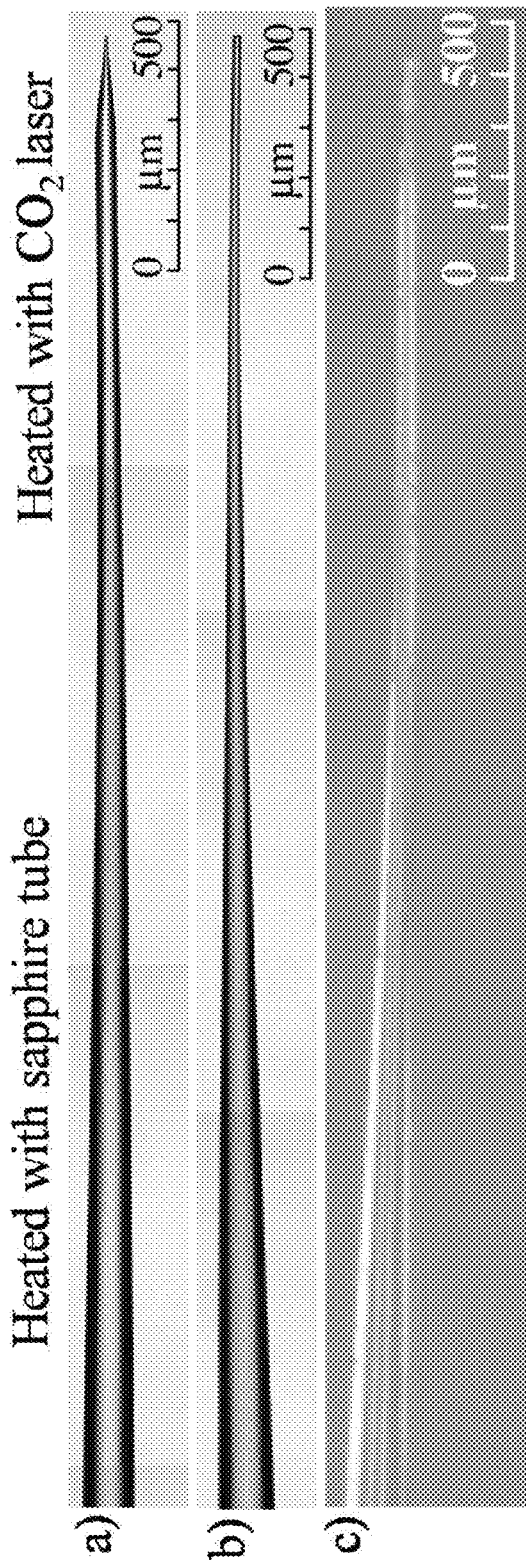
FIGS. 8A and 8B are, respectfully, brightfield images of a sharp and a flat microneedle prepared according to processes of the invention.
FIG. 8C is a color microscope image of a sharp microneedle of an embodiment of the invention, shown delivering red laser light.

FIGS. 8A and 8B are brightfield images of a sharp and a flat microneedle prepared according to processes of the invention, respectively. FIG. 8C is a color microscope image of a sharp microneedle delivering red laser light near the tip ($\lambda$=633 nm).

Eight flat microneedles (F1-F8) and twelve sharp microneedles (S1-S12) were manufactured. Microneedles F1 through F4 were manufactured as explained in Step I of the above-described process. Microneedles F5 through F8 were manufactured by flat-cleaving optical fibers and had no melt-drawing applied. Microneedles S1 through S10 were manufactured by the two-step melt-drawing process (Step I and II) described above. Microneedles S11 and S12 were manufactured using only $CO_2$ laser heating (Step II) as described above. Microneedles S11, S12, and F5, were made from single-mode fiber (8±0.7 μm core/125±0.7 μm cladding), while all other microneedles were manufactured from multi-mode optical fiber (125±5 μm silica core/140+2/−5 μm silica cladding).

For flat microneedles with linearly varying cross-sectional diameters, an average diameter ($d_{AVG,FLAT}$) can be defined by Eq. (1):

$$d_{AVG,FLAT} = \frac{d_{BASE} + d_{TIP}}{2} \quad (1)$$

In Eq. (1), the base diameter ($d_{BASE}$) is the thickness of the microneedle 3 mm from its tip. The tip diameter ($d_{TIP}$) is the diameter of the tip. The taper angle of the flat microneedles is calculated by Eq. (2):

$$\alpha_T = \tan^{-1}\left(\frac{d_{BASE} - d_{TIP}}{2L}\right) \quad (2)$$

In Eq. (2), L is the unsupported length and was equal to 3 mm (±0.1 mm uncertainty) for all microneedles.

For sharp microneedles, the two taper angles are given in Eq. (3) and Eq. (4):

$$\alpha_{T1} = \tan^{-1}\left(\frac{d_{BASE} - d_{INF}}{2(L - L_{TIP})}\right) \quad (3)$$

$$\alpha_{T2} = \tan^{-1}\left(\frac{d_{INF} - d_{TIP}}{2L_{TIP}}\right) \quad (4)$$

The inflection diameter ($d_{INF}$) is the thickness of the microneedle at the junction of the first and second taper. Tip length ($L_{TIP}$) is the length of the second taper for sharp microneedles. In the second taper section of the microneedle, the taper angle ($\alpha_{T2}$) increases. The distance from the base to the junction point of two different tapers ($L-L_{TIP}$) equaled 88% to 94% of the full length of the microneedle.

For the sharp microneedles, $d_{AVG,SHARP}$ was defined as in Eq. (5):

$$d_{AVG,SHARP} = \frac{d_{BASE} + d_{INF}}{2} \quad (5)$$

For calculation of sharp microneedle average diameter, $d_{TIP}$ is replaced by $d_{INF}$ because the first taper section ($L-L_{TIP}$) is much larger than the second taper section ($L_{TIP}$).

Tables 3 and 4 include the values for geometric parameters of some exemplary microneedles (F1-F8 and S1-S12) according to the invention. For microneedles S11 and S12, $\alpha_{T2}$ provided an equivalent average value for taper angle. The actual taper angle varied along the length of the second taper due to the non-linear behavior of the decrease in diameter.

TABLE 3

Geometric Parameters of Flat Microneedles

| Microneedle | Base Diameter $d_{BASE}$ [μm] | Average Diameter, $d_{AVG}$ [μm] | Tip Diameter, $d_{TIP}$ [μm] | Taper Angle $\alpha_T$ [°] |
|---|---|---|---|---|
| F1 | 61 | 35 | 9 | 0.5 |
| F2 | 103 | 60 | 17 | 0.8 |
| F3 | 113 | 65 | 18 | 0.9 |
| F4 | 132 | 75 | 18 | 1.1 |
| F5 | 125 | 125 | 125 | 0 |
| F6 | 136 | 136 | 136 | 0 |
| F7 | 136 | 136 | 136 | 0 |
| F8 | 139 | 139 | 139 | 0 |

TABLE 4

Geometric Parameters of Sharp Microneedles

| Microneedle | Base Diameter $d_{BASE}$ [μm] | Inflection Diameter $d_{INF}$ [μm] | Average Diameter, $d_{AVG}$ [μm] | Tip Length $L_{TIP}$ [μm] | Tip Diameter, $d_{TIP}$ [μm] | First Taper Angle, | Second Taper Angle, |
|---|---|---|---|---|---|---|---|
| S1 | 63 | 24 | 44 | 207 | 3 | 0.4 | 2.9 |
| S2 | 88 | 22 | 55 | 189 | 5 | 0.7 | 2.7 |
| S3 | 105 | 22 | 63 | 164 | 4 | 0.8 | 3.1 |
| S4 | 120 | 14 | 67 | 221 | 4 | 1.1 | 1.4 |
| S5 | 120 | 14 | 67 | 201 | 4 | 1.1 | 1.5 |
| S6 | 119 | 22 | 70 | 190 | 4 | 1.0 | 2.7 |
| S7 | 125 | 15 | 50 | 221 | 4 | 1.1 | 1.4 |
| S8 | 104 | 41 | 73 | 175 | 8 | 0.6 | 5.4 |
| S9 | 119 | 27 | 73 | 211 | 4 | 0.9 | 3.2 |
| S10 | 121 | 56 | 89 | 262 | 2 | 0.7 | 5.9 |
| S11 | 125 | 125 | 125 | 308 | 8 | 0.0 | 10.7 |
| S12 | 125 | 125 | 125 | 365 | 6 | 0.0 | 9.3 |

Figure 22:
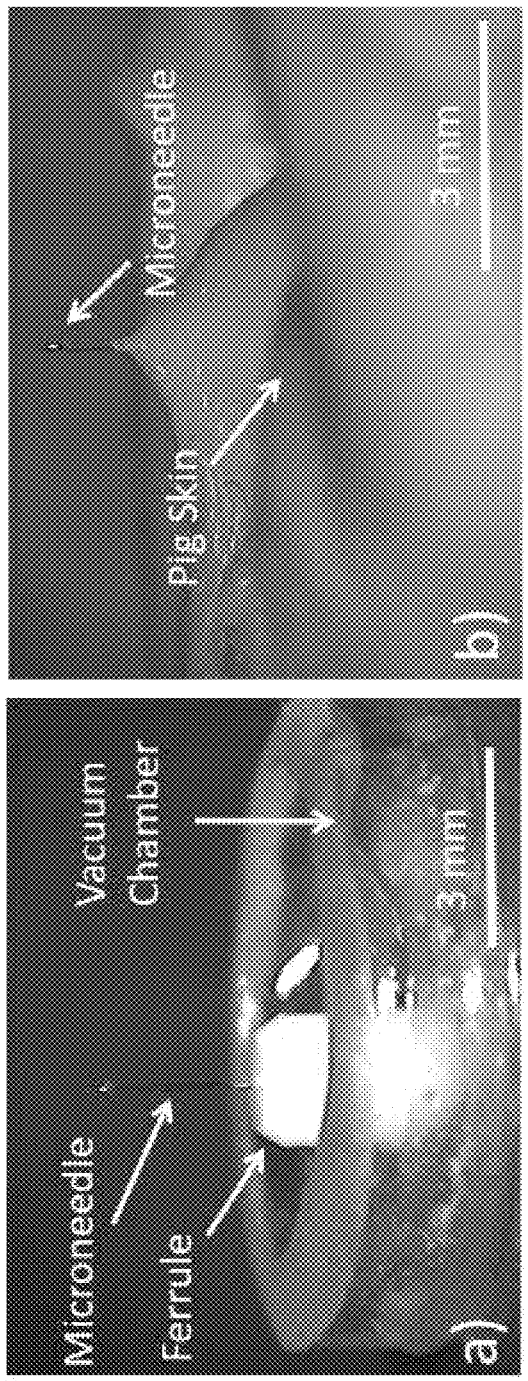
FIGS. 22A and B are photographic images of a) Vacuum chamber, ferrule, and the fiberoptic microneedle; b) Fiberoptic microneedle penetrating 2 mm thick pig skin.

The 20 microneedles were tested for skin penetration capability by inserting the needles through skin samples that were fixed above a U-Channel. All of these microneedles had the same unsupported length of 3 mm (i.e., the microneedles were fixed inside a steel tube with a 3±0.1 mm unsupported length by application of adhesive on their base). The microneedles were positioned 1 mm or less away from the surface of the skin and then translated into the skin with a velocity of 0.5 mm/sec until penetration or buckling occurred. Microneedle displacement and penetration force were measured during insertion into the pig skin samples using a BOSE™ Electroforce™ 3100 mechanical testing instrument. This instrument has 1.5 μm displacement resolution over its 5 mm range. FIGS. 22A and B are photographic images of a) Vacuum chamber, ferrule, and a fiberoptic microneedle; b) Fiberoptic microneedle penetrating 2 mm thick pig skin.

Flat microneedles F5 through F8 and sharp microneedles S8 through S12 were able to penetrate pig skin. For sharp microneedles ($d_{TIP}$=2-8 μm), successful penetration was achieved by microneedles with $d_{AVG}$=73-125 μm, or said another way, a minimum average diameter of 73 micron and a maximum tip diameter of 8 micron. Flat microneedles prepared by the flat-cleaving process also successfully penetrated skin with $d_{AVG}$ between 125 to 139 μm. Flat microneedles, which had larger tip diameters, required a minimum average diameter of 125 micron in order to penetrate through pig skin samples. Flat microneedles that were able to penetrate were larger in average diameter (125 to 139 μm) in comparison to sharp microneedles (73 to 125 μm).

The taper angle of the microneedles was low ($\alpha_{T1}$=0-1.1°). Thus, the critical buckling force, $F_{CR}$ of the microneedle can be approximated by Euler's buckling formula for a cylindrical column with one fixed end and one free end, which is given in Eq. (6);

$$F_{CR} = \frac{E\pi^3 d_{AVG}^4}{256L^2} \quad (6)$$

In Eq. (6), E is the elastic modulus of silica. This formula indicates that $F_{CR}$ is dependent to the fourth order on $d_{AVG}$. Thus, a 50 percent reduction in the thickness to produce less invasive microneedles limits the mechanical strength by a factor of 16.

Two attributes were likely to contribute to the success of the sharper yet thinner microneedles. First, the range of peak forces that occurred during penetration of sharp microneedles (234±110 mN to 646±6 mN) was much less than the range for flat microneedles (692±6 mN to 1350±110 mN). Second, the change in the force during penetration was steadier for sharp microneedles compared to the flat microneedles.

This is because sharp microneedles likely penetrated through the skin by forming a planar mode I crack as explained in the literature. See Shergold 2005. During insertion of microneedles S8, S10, S11, and S12, the force increased and decreased without any sudden drops. Flat microneedles likely penetrated the skin by forming a mode II ring crack, and the microneedles penetrated through the skin with jerky movements which caused sudden drops in the force. See Shergold 2005. Thus, our experiments showed that the change in penetration mechanics is evident even though the diameters of the microneedles used in this paper (ranging from about 73 to 139 μm) were much smaller than the punches (300 to 600 μm) used in the Shergold experiments.

For clinical applications, other considerations are instructive. Besides discomfort and bleeding, another harmful side effect might be caused by small silica particles that break off from the microneedles inside or underneath the patient's skin. To ascertain the possibility of microneedle breakage, images of microneedles before and after insertion were recorded and compared. Flat microneedles that successfully penetrated pig skin samples sustained no visible microscopic damage. Sharp microneedles S9, S10, and S12 with smaller tips ($d_{TIP}$=2-6 μm) were damaged along their tips. In contrast, microneedles S8 and S11, which had relatively larger tip diameters ($d_{TIP}$=8 μm), remained intact during and after penetration of skin. Accordingly, the geometry of S8 and S11 may be preferred for optimizing the shape of the fiberoptic microneedles for safe clinical use.

Embodiments of the present invention comprise a microneedle and a device for supporting the microneedle during use to facilitate penetration of the needle into skin and without breakage (or other failure) of the needle during use, otherwise referred to as a hand-held microneedle injection device. More than one needle can be supported by the tool, however, a preferred embodiment comprises a single needle approach.

Figure 2:
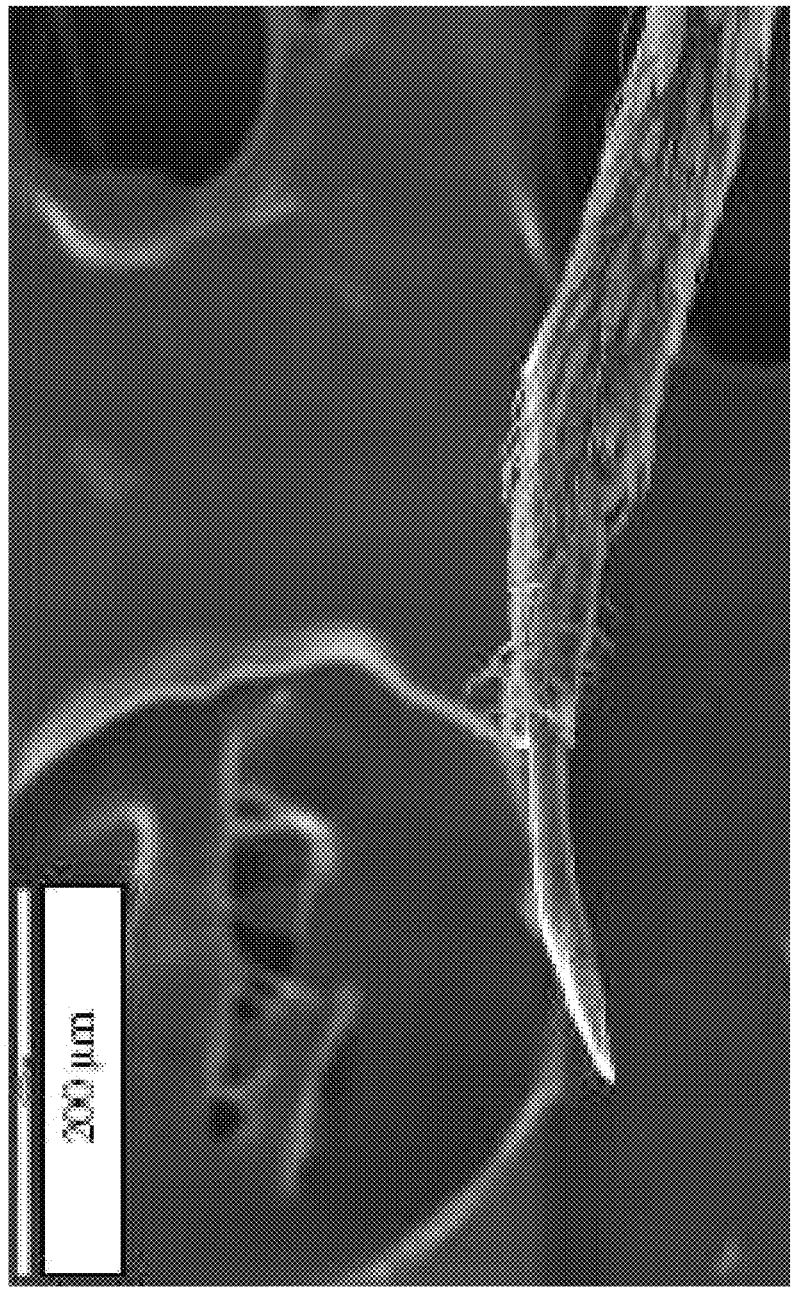
FIG. 2 is a photographic image of a mosquito fascicle and supporting labium.
Figure 9:
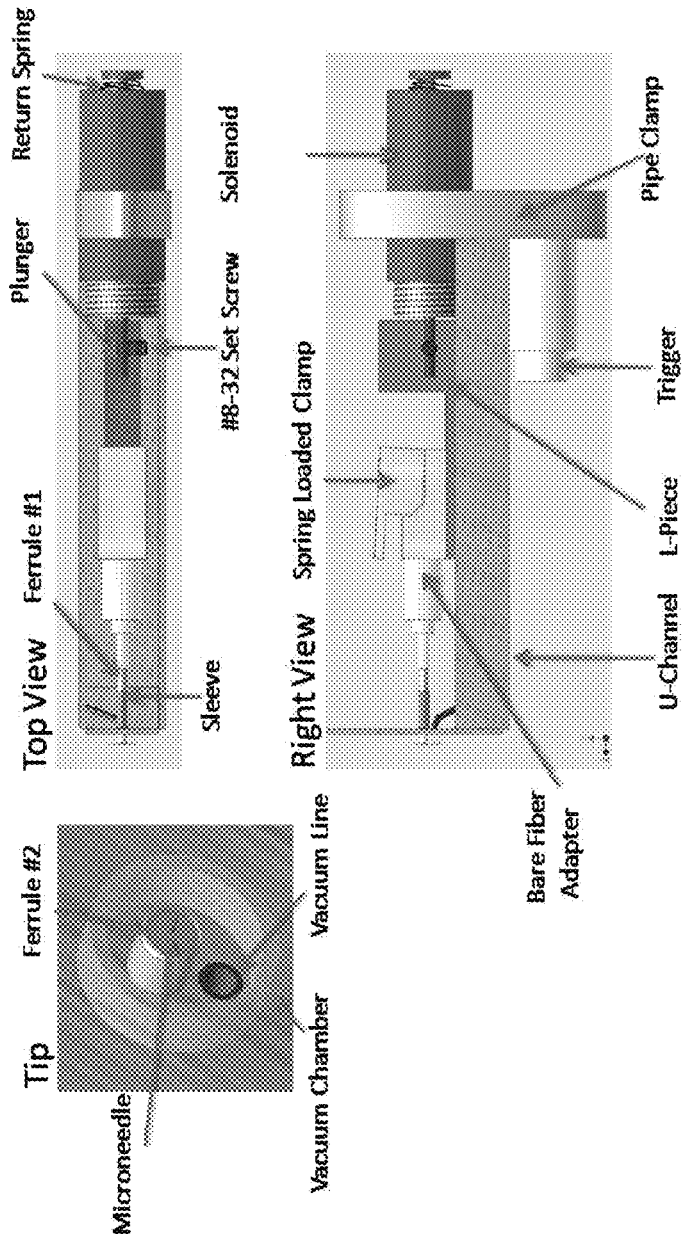
FIG. 9 is a schematic diagram of a hand-held microneedle insertion device according to an embodiment of the invention.
Figure 18:
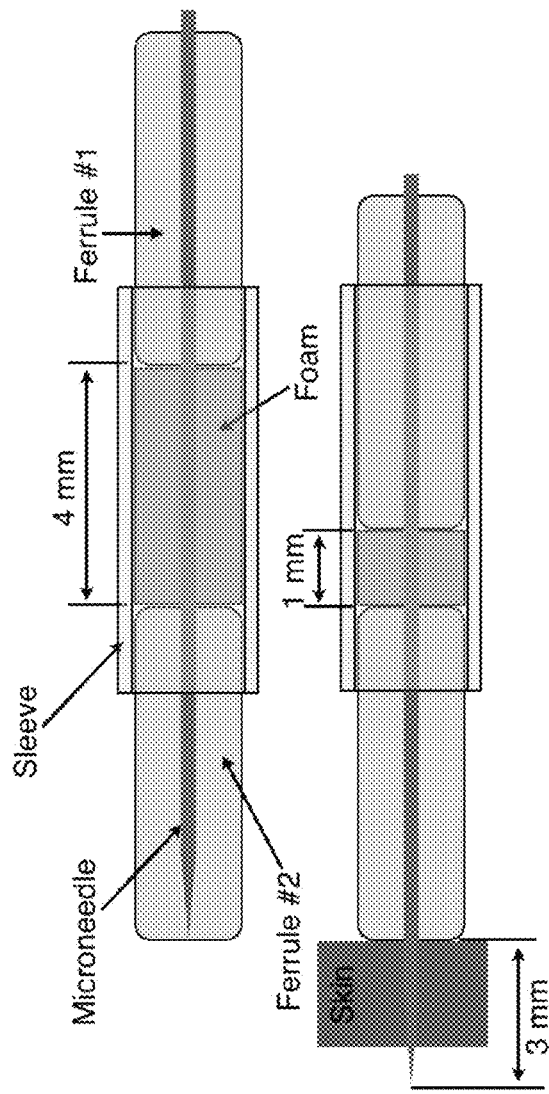
FIG. 18 is a schematic diagram showing an embodiment of the invention which provides a microneedle device (e.g., a fiberoptic microneedle device or FMD).
Figure 19:
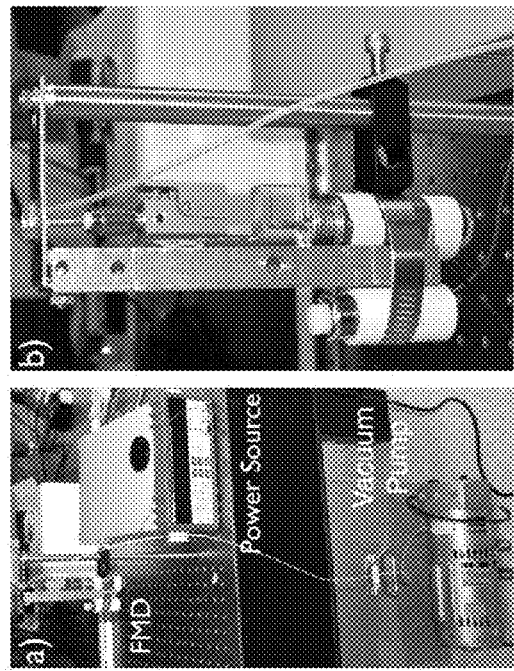
FIGS. 19A and B are photographic images showing a) Overview of an FMD setup and b) Close-up image of an embodiment of the device.

More particularly, FIG. 18 shows an embodiment of the invention which provides a microneedle device (e.g., a fiberoptic microneedle device or FMD) having a push type, spring return solenoid for pushing the microneedle into skin. A magnetic coil inside this solenoid translates a circular pin called the plunger towards the skin when a 12V 3A DC current is applied. The plunger stops moving when the return spring on the proximal end of the solenoid is compressed. An L-shaped piece connects a bare fiber adaptor to the solenoid. A bare fiber adaptor is a special optical device that is usually used to connect an uncoated and unjacketed optical fiber to an optical system. In embodiments, the bare fiber adaptor is used to hose the optical fiber with the microneedle on its tip. The proximal end of the adaptor is consisted of a zirconia optical ferrule (Ferrule #1) with a 125.5 mm inner diameter and 2.5 mm outer diameter. This ferrule is inserted inside a fiberoptic sleeve from the proximal side. Ferrule #1 slides inside this sleeve freely when the adaptor is moved. Another ferrule (Ferrule #2) is inserted into the sleeve from the distal side of the fiberoptic sleeve. Fiberoptic sleeve aligns the two ferrules in the device to be coaxial. When the solenoid is activated, the fiberoptic ferrule 1 moves closer to the fiberoptic ferrule 2, and the fiber slides through both of them. The tip of the fiber extends away from the distal end of ferrule #2 exposing 3 mm of optical fiber including the microneedle on the tip of the fiber. A cylindrical piece of foam is placed inside the fiberoptic sleeve in order to provide the mechanical strengthening effect. An illustration of the mechanism is given in FIG. 2. A plastic brim was placed around the ferrule in order to produce a vacuum chamber. A schematic diagram of another single needle guide and supporting device is shown in FIG. 9. Further, FIGS. 19A and B provide photographic images showing a) Overview of an FMD setup and b) Close-up image of an embodiment of the device.

To verify the efficacy of the hand-held FMD, microneedles supported by the FMD were inserted into skin samples. More particularly, skin samples 2 mm thick were prepared from the fresh ex vivo abdominal pig skin which was provided by the Virginia-Maryland Regional College of Veterinary Medicine. These skin samples were either clamped around the vacuum chamber of the FMD or just laid loosely on top. A vacuum was applied for 8 seconds which caused the skin to fold into the chamber and stretch over the optical ferrule. The microneedle was pushed against the skin by actuating the solenoid.

The FMD successfully injected the microneedles through the pig skin samples 10 out of 10 times, when the skin was fixed around the vacuum chamber using clamps prior to application of the vacuum. Further, the FMD injected the microneedles through the skin 8 out of 20 times when the skin was loose or not fixed, with the microneedles either buckling or pushing the skin away from the vacuum chamber without penetration through the skin samples in the remaining 12 out of 20 times.

Figure 10:
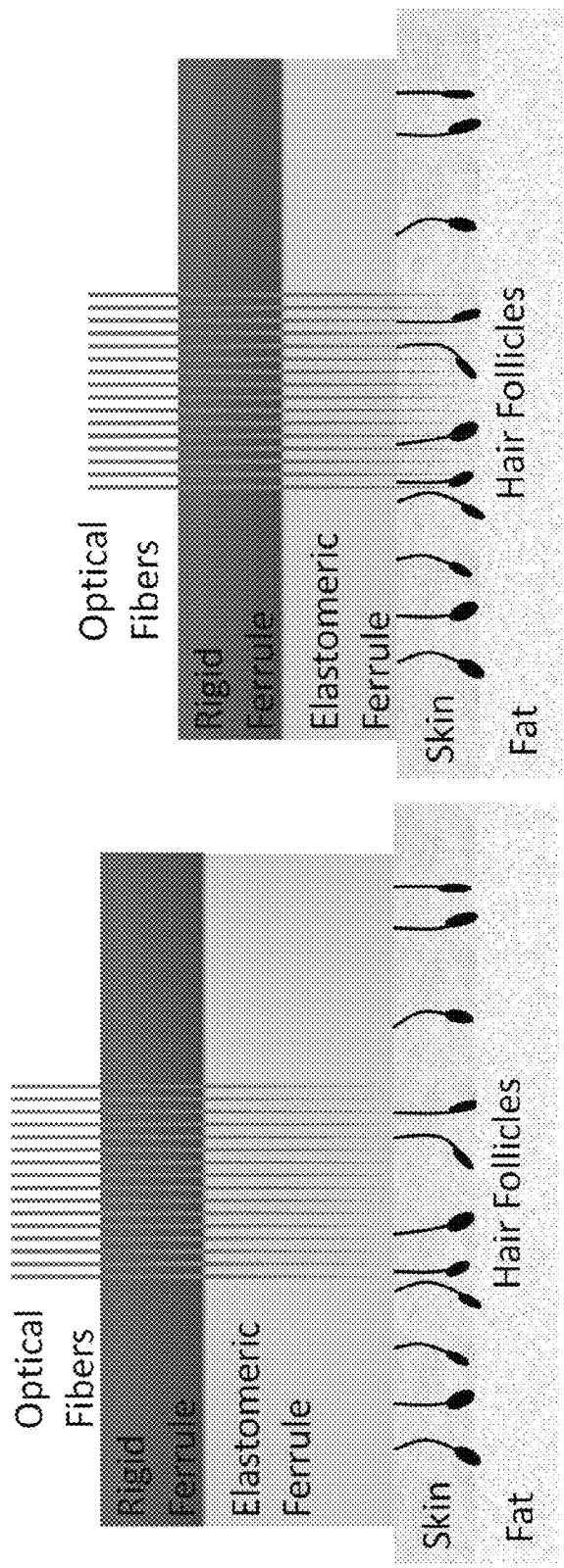
FIG. 10 is a schematic diagram of a microneedle insertion device according to embodiments of the invention.

As shown in the schematic diagram of FIG. 10, other devices for supporting one or more microneedles according to the invention during insertion into skin are also included within the scope of the invention. For example, an array of needles can be used to allow greatly increased light penetration in skin to enable a new regime of deep-tissue light-based therapeutic procedures. In embodiments, a device comprises an array of optically transparent fibers (about 40 microns in outer diameter at the tip) which are guided into a patient's tissue by an elastomeric support ferrule (bushing).

It is known that a mechanical strengthening mechanism for microneedles can be achieved by limiting their lateral movement. See, Khumpuang, S., R. Maeda, and S. Sugiyama, "Design and fabrication of a coupled microneedle array and insertion guide array for safe penetration through skin," in Micromechatronics and Human Science, 2003, MHS 2003: Proceedings of 2003 International Symposium, the disclosure of which is incorporated by reference herein in its entirety. Surrounding the microneedles with an elastic medium such as a polymer may be effective in preventing the microneedles from breaking while being forced into the skin tissue. The positive effect of this mechanism was calculated theoretically. The elastomeric ferrule can optionally be used in conjunction with a rigid ferrule and/or sandwiched between two or more rigid ferrules. The rigid ferrule need not be of a certain rigidity, so long as it is more rigid than the elastomeric portion of the device.

Critical buckling force is the limiting factor for the mechanical strength of these needles because it is the most common mode of failure for long and slender objects under axial stress, such as these microneedles when they are being forced into in vivo tissues. For the simplicity of calculations, the microneedles will be modeled as straight cylindrical columns. The critical buckling force for a straight Euler column is given by formula (7) below:

$$P_{CR} = \frac{C\pi EI}{l^2} \quad (7)$$

where $P_{CR}$ is the critical buckling force, E=50 GPa is the elastic modulus of the microneedle material (Silica in our case) and I is the inertial moment of the cross section. C is a constant that changes between 0.25 and 4 and is determined by the end conditions of the column. If one end of the needle is fixed to the rest of the fiber which is held tightly inside a fiber chuck and the other end is free as it is being injected to the skin, then C can be 0.25.

In embodiments of the invention, surrounding the microneedle, or microneedles in an array of microneedles, with an elastic medium such as a polymer will increase the critical buckling force by limiting the lateral movement of the microneedle. It is assumed here that the elastic medium will act similar to a series of springs with a spring constant that equals the elastic modulus of the material.

The buckling equation for a straight Euler column with a continuous elastic restraint is given in formula (8) below as (See, Wang, C. M., Wang C. Y., Reddy, J. N., "Exact Solutions for Buckling of Structural Members," 2004 CRC Series in Computational Mechanics and Applied Analysis, the disclosure of which is incorporated by reference herein in its entirety):

$$\frac{d^4w}{dx^4} + \alpha\frac{d^2w}{dx^2} + \xi w = 0 \quad (8)$$

where x and w are the non-dimensionalized variables $$x = \bar{x}/L \text{ and } w = \bar{w}/L \quad (9)$$

where L=3 mm is the length of the needle, $\bar{x}$ is the vertical distance from the base, and $\bar{w}$ is the transverse displacement perpendicular to the axis. The buckling force is calculated from the critical load parameter, which is given as;

$$\alpha = P_{CR}L^2/EI \quad (10)$$

The restraint stiffness is calculated as $$\xi = cL^4/EI \quad (11)$$

The value c=2 GPa is the elastic modulus of the surrounding medium, which is a type of polyester, e.g., Nylon.

The range of forces that is needed to penetrate the skin with microneedles has been reported. See, Davis, S. P., et al., "Insertion of microneedles into skin: measurement and prediction of insertion force and needle fracture force," Journal of Biomechanics, 2004, 37(8): pp. 1155-1163, the disclosure of which is incorporated by reference herein in its entirety.

Figure 11:
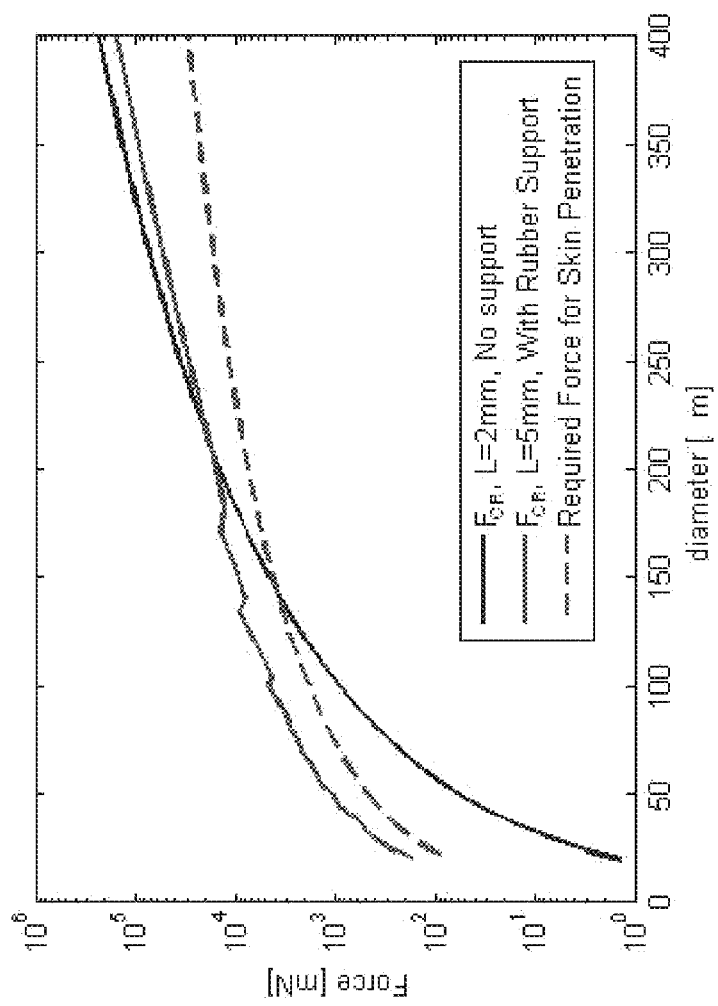
FIG. 11 is a graph of the critical buckling force of microneedles according to the invention of 2 mm and 5 mm in length (with and without additional support means) and the range of forces needed for inserting various diameter needles into skin.

FIG. 11 is a graph showing the minimum and maximum forces that might be needed to penetrate skin, the critical force for buckling of a straight Euler column (without support), and the critical force for buckling of a straight Euler column with a continuous elastic restraint (additional external support means). These forces were calculated for different diameters of microneedles and nanoneedles.

For the case of a straight needle with no elastic restraint, the critical force is quite small. For a 1 μm diameter needle, the critical buckling force is three orders of magnitude smaller than the force needed to penetrate skin. It can be seen from FIG. 11 that a perfectly straight needle made from silica has to be around 100 μm in diameter to be able to penetrate skin. This is the same size as a small optical fiber or small wood splinter, which are known to penetrate skin easily and inflict pain. But the desired condition for the needle is to not induce pain to the patient during insertion, so the diameter of the needle has to be much smaller.

To provide a pain-free needle and avoid exceeding the critical buckling force, the needle can be supported by an elastic medium as it is being injected to the skin. This can be achieved in many ways, such as deposition of a liquid polymer around the needles or using a polymer template with small holes of precise dimensions.

The theoretical advantage of such an application is demonstrated by the increased critical stress due to the elastic restraint. The critical force for buckling exceeds the force needed for penetration, even for a 100 nm diameter. A simulation was performed to estimate the critical buckling force of a 5 mm long microneedle inside an elastic support medium ($E_S$=10 MPa) which is reasonably obtained with a soft rubber. For diameters under 200 μm, the critical buckling force of the longer (5 mm) supported microneedle is greater than the buckling force for a shorter (2 mm) unsupported needle. The elastic medium is much softer than the actual needle, but owing to the small diameter of the needle, the surrounding medium acts very stiff relative to the needle, and we are able to increase the critical buckling force by more than 10× at 40 μm diameter. Additionally, the critical force for buckling of the supported microneedle exceeds the force needed for skin penetration by a factor of ~3× for all diameters used in the simulation. Thus, small and densely packed sub-micron needles with an elastic support can have sufficient strength to penetrate skin without fracture or other failure.

Figure 12:
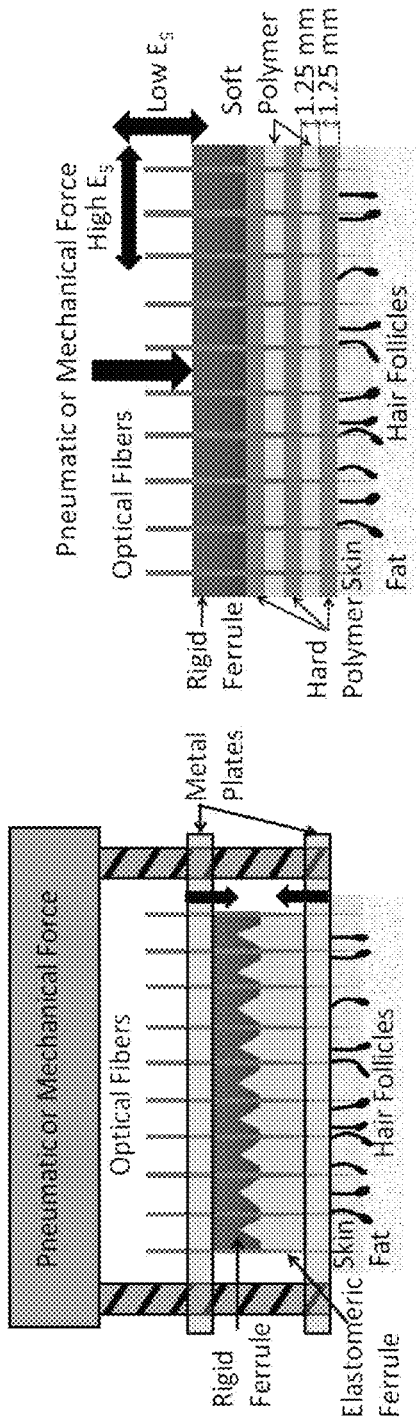
FIG. 12 provides schematic diagrams showing embodiments of the invention that comprise an array of microneedles supported along their length by rigid and soft ferrules during insertion of the needles into skin.

Once the microneedle system is fabricated, the clinician places the elastomeric guidance ferrule in contact with the patient's skin. Mechanical compression induced by the clinician or an automatic control system (e.g., vacuum pump with adjustable pressure/force) will cause the elastomeric ferrule to compress or collapse and pull the rigid ferrule (and fibers)

toward the skin. As shown in FIGS. 10 and 12, the distal (usually tapered, but not required) ends of the fibers will penetrate into the skin guided by the elastomeric ferrule.

To maximize the smoothness of the operation and treatment efficacy, a feedback and control mechanism with stress/strain sensors can be applied to monitor penetration depth and force. When the pressure/vacuum/displacement sensor detects a critical threshold value, the laser source can be turned on and energy provided to the fibers and delivered into the skin for a given amount of time to provide an appropriate radiative dose.

In embodiments of systems of the invention, one or more microneedles are fixed to a rigid ferrule (straight bushing) and extend unfixed throughout the full-thickness of an adjacent elastomeric ferrule. As the elastomeric ferrule is compressed between the rigid ferrule and a tissue surface, such as skin, microneedle tips exit the elastomeric ferrule and penetrate into adjacent tissue. The elastomeric ferrule provides lateral support for the microneedles, increasing the critical buckling force, similar to mosquito bite mechanics.

The rigid ferrule may be forced toward the tissue surface directly using human-applied force or with an alternative mechanism such as vacuum force. If the elastomeric ferrule is fabricated with a porous, open-celled elastomer such as foam, vacuum pressure can be used to collapse the pores, inducing needle insertion into skin. Additionally, vacuum pressure may help seal the skin surface against the elastomer, minimizing shear stress at this interface.

The force exerted on skin by the microneedles is negligible; however, the force needed to compress the elastomeric ferrule against tissue must be below skin pain and damage thresholds. FMD designs capable of preventing excess force on the subject include the two designs shown in FIG. 12. The schematic diagram at the left of FIG. 12 provides the elastomeric ferrule between two rigid metal plates, which is compressed during use, of the device. In embodiments, the force needed to deform the elastomeric ferrule is not be applied on the skin but rather on the metal plates using a pneumatic or screw-driven linear actuator attached to opposite sides of the square plates. Alternatively, embodiments can comprise as the material for the elastomeric ferrule one with directionally dependent elastic moduli, preferably a high elastic modulus in the lateral direction E>100 MPa, but a much smaller elastic modulus E<1 MPa in the vertical direction. Such a material can be achieved by composite (layered) manufacturing as shown in the schematic diagram shown on right in FIG. 12.

In a specific embodiment of FMD, which is especially useful for hair removal applications, the needles cover approximately a 1 cm$^2$ surface area, the needles are configured to be capable of attaining a 2 mm needle insertion depth, and comprise about 30 needles/cm$^2$ based on hair follicle length and density. The device optionally comprises a rigid ferrule, which can be made of machined aluminum (5 mm thick) and an elastomeric ferrule which can be comprised of rubber or foam (1-20 mm thick). Precision drilled holes are made through both materials to hold the optical fibers. Fibers are manually inserted into holes, positioned with our stereo microscope, and fixed to the rigid ferrule with epoxy. A pneumatic chamber can be used to cause FMD compression against the skin surface.

For dermatological applications, the devices may be placed against a patient's skin. Mechanical compression causes the fiber needles to slide through the ferrule and painlessly penetrate the skin, similar to the dynamics of a mosquito bite. The fiber tips may be positioned at desirable target positions (potentially >2 mm deep) within tissue. Subsequent application of laser energy into the proximal end of fibers will be transmitted efficiently to the target tissue surrounding the fiber tips, thereby inducing desirable photothermal, photomechanical, or photochemical damage to the intended target.

In preferred embodiments, the clinician places the ferrule in contact with the patient's skin and the distal end of the fibers slide through the ferrule, elastomeric material, and into the skin. A feedback and control mechanism monitors treatment for penetration depth and force using a complementary series of stress/strain sensors. Diffuse optical tomography (DOT) may then be used to optically identify and characterize tissue structures beneath the epidermis layer, such as cancerous cells, hair follicles, freckles, tattoo particles, blood vessels, epidermal/dermal junctions, and dermal/adipose junctions.

Indeed, embodiments of the invention can be coupled with any optical imaging system for diagnostic or therapeutic use. Sub-dermal targets can be identified using any optical molecular imaging technique, such as OMT, OCT (Optical Coherence Tomography), bioluminescence imaging, Diffuse Optical Tomography (DOT), and fluorescence tomography to name a few.

Additionally, light can be introduced to certain fibers and detected by others, with the process implemented sequentially and/or in parallel as a function of wavelength. Moreover, laser therapeutics is thus further enabled with the proposed device in that laser irradiation can be directed into the proximal end of selected individual fibers to induce photothermal, photomechanical, or photochemical damage to target tissue structures identified using DOT. In concert with DOT, treatment can thus be more specified to the target area, therefore dramatically reducing collateral damage and enabling reduced pain during treatment and faster wound healing. See, Kaushik, S., et al., "Lack of pain associated with microfabricated microneedles," Anesthesia and Analgesia, 2001, 92(2): p. 502-504, the disclosure of which is incorporated by reference herein in its entirety. Embodiments of the invention have potential market implications in cosmetic surgeries, oncology treatments, dermatology treatments, and alternative medicine protocols.

The microneedles, with or without a skin insertion tool, and the microneedle systems of embodiments of the invention can be used for numerous clinical applications.

Figure 13:
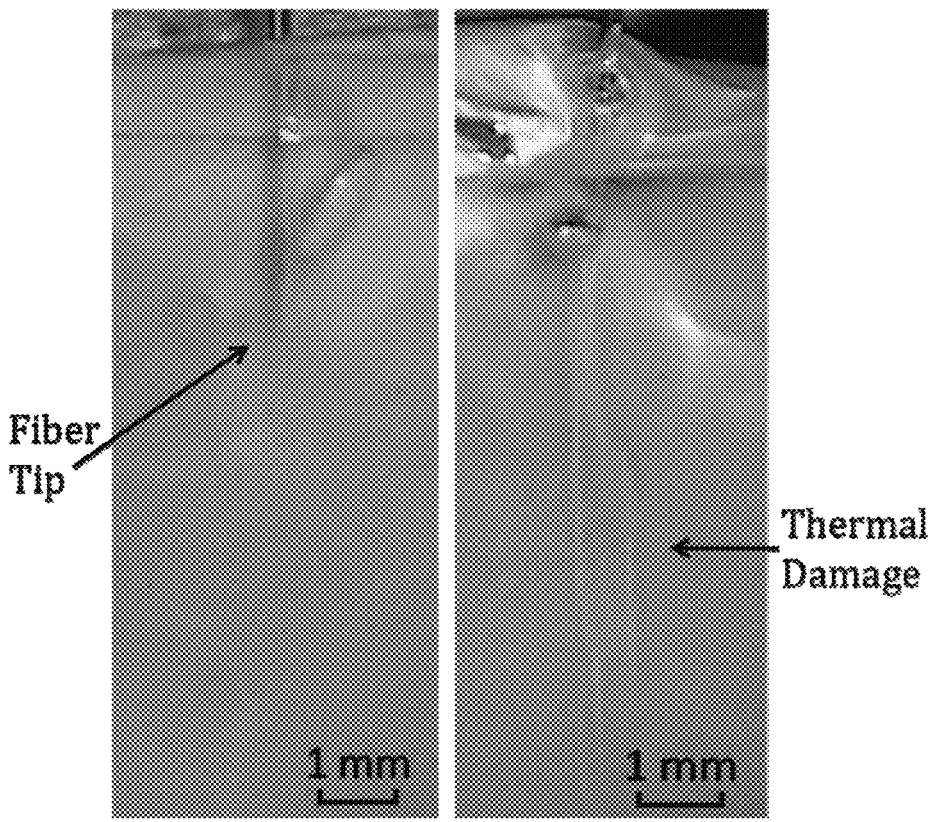
FIG. 13 are photographic images showing photothermal-induced denaturation in gelatin tissue phantoms using a microneedle light delivery system according to the invention.

FIG. 13 shows photothermal-induced denaturation in gelatin tissue phantoms using a microneedle light delivery system. The microneedle was inserted into the gelatin and a 1064 nm wavelength laser (~0.1 W continuous wave) was focused into the core of the proximal end of the fiber. Due to absorption of photons by the water in the phantom along the direction of the light propagation, heat was generated which melted and denatured the gelatin to a depth of approximately 5 mm.

More specifically, the microneedles were used to ablate the tissue phantom (gelatin) with a focused high power laser. The microneedles were inserted into gelatin and a 5 W fiber laser with a wavelength of 1064 nm was focused into the core of the optical fiber at its other end, which was straight cleaved. The needle at the tip increased the light intensity per area and the intense laser light tunneled through the gelatin. The microneedle is located at the left side of the images in FIG. 13. It is embedded inside a cube of gelatin that is placed between two glass cover slides in order to minimize spurious reflection. The top image shows the start of the experiment. When the laser is activated, heat emanating from the tip of the needle melts the gelatin along the direction of the needle axis. The resulting shape of gelatin is shown in the bottom image. The red light inside the optical fiber is a guide laser, which makes it possible to see the location of the infrared beam.

Laser therapeutics can be used to direct laser irradiation into the proximal end of selected individual fibers to induce photothermal, photomechanical, or photochemical damage to targeted tissue structures identified using DOT. Light can be delivered to deeper targets because of the insertion of the fibers into skin. Specificity of the treatment can be enhanced using DOT imaging and less collateral damage potentially means less pain during treatment and faster wound healing process. Further, DOT may provide feedback on success of the treatment.

In photothermal therapeutics, successful treatment outcome often depends on a desired temperature increase in selected tissue regions resulting in destruction of targeted chromophores or regions, while maintaining temperature below the damage threshold in non-targeted tissue regions, a process called selective photothermolysis. See, Anderson, R. R. and J. A. Parrish, "Selective Photothermolysis—Precise Microsurgery by Selective Absorption of Pulsed Radiation," Science, 1983, 220(4596): p. 524-527, the disclosure of which is incorporated by reference herein in its entirety.

Laser-based hair removal, for example, benefits from selective heating of melanin in hair follicles, while minimizing heating in surrounding skin. Selective thermal damage of pigmented target structures occurs when sufficient fluence is delivered during a time equal to or less than the thermal relaxation time $\tau_r$ of the target, where $\tau_r$ is defined as the time required for the central temperature of the target to decrease by 50%. For long pulses (duration$>>\tau_r$) nonspecific damage will result due to significant heat transfer during the pulse.

Rate of temperature increase dT(r,z)/dt in tissue at position (r,z) due to light absorption is given by, $$\frac{dT(r,z)}{dt} = \frac{\mu_a \Phi}{\rho c} \quad (1)$$

and is dependent on local tissue absorption coefficient ($\mu_a$), local optical fluence ($\Phi$), tissue density ($\rho$), and specific heat capacity (c).

Local fluence in tissue may be approximated by:

$$\Phi(z) = \Phi_0 e^{-\mu_{eff} z} \quad (2)$$

where $\Phi_0$ is the irradiance on the surface, z is tissue depth, and $\mu_{eff}$ is effective attenuation coefficient which depends on tissue optical properties. The optical penetration depth, defined as $1/\mu_{eff}$, is the tissue depth at which fluence has exponentially decayed to 37% of the incident surface irradiance, and is approximately 750 μm in skin at a wavelength of 700 nm. See, Anderson, R. R. and J. A. Parrish, "The Optics of Human-Skin," Journal of Investigative Dermatology, 1981, 77(1): p. 13-19, the disclosure of which is incorporated by reference herein in its entirety.

Figure 14:
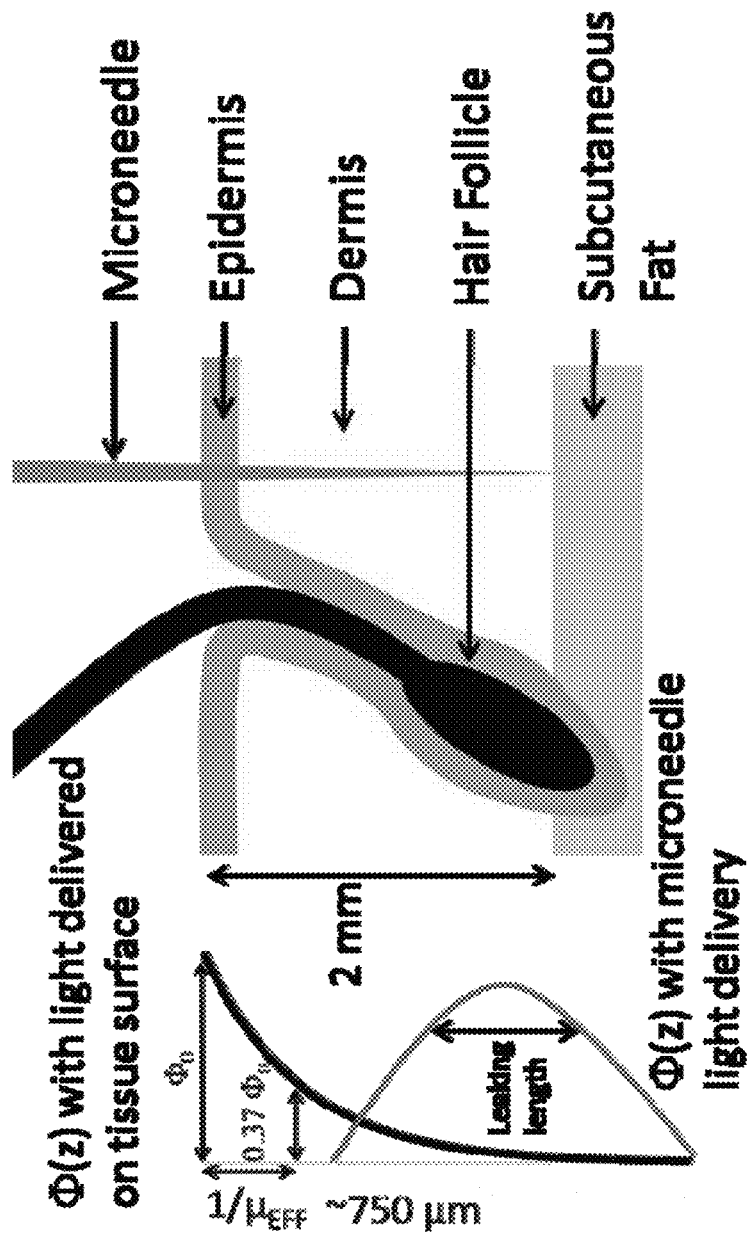
FIG. 14 is a graphical illustration of $\Phi(z)$ and optical penetration depth in skin using current commercial laser treatment procedures (beam directly delivered to skin surface).

FIG. 14 (left) provides a graphical illustration of $\Phi(z)$ and optical penetration depth in skin using current commercial laser treatment procedures (beam directly delivered to skin surface). As shown in the graph, very little light reaches the deep portions of the hair follicle where light is needed most.

One example of the application of the invention is for laser-based hair removal. Laser-based hair removal has recently received attention because of its noninvasive nature, fast results, and potential for permanence. Long term results have been described with Alexandrite lasers (755 nm) which use melanin in the hair follicle as a chromophore for selective photothermolysis. See, Nanni, C. A. and T. S. Alster, "Long-pulsed alexandrite laser-assisted hair removal at 5, 10, and 20 millisecond pulse durations," Lasers in Surgery and Medicine, 1999, 24(5): p. 332-337, the disclosure of which is incorporated by reference herein in its entirety.

Skin anatomy and tissue optics are such that it is difficult to achieve the light levels needed for selective photothermolysis of the deep portions of hair follicles which can be greater than 2 mm under the skin surface. The epidermis contains additional melanin through which light must pass to reach the follicle. Ideally follicles should be damaged without much epidermal injury. Approximating hair follicles as a cylinder, their thermal relaxation times are in the range of about 10-100 msec for diameters between about 100-300 μm. See, Campos, V. B., et al., "Ruby laser hair removal: Evaluation of long-term efficacy and side effects. Lasers in Surgery and Medicine," 2000, 26(2): p. 177-185, the disclosure of which is incorporated by reference herein in its entirety.

However the thermal relaxation for the epidermal melanin layer (~50 um thickness) is approximately 3-10 msec. See, Grossman, M. C., et al., "Damage to hair follicles by normal-mode ruby laser pulses," Journal of the American Academy of Dermatology, 1996, 35(6): p. 889-894, the disclosure of which is incorporated by reference herein in its entirety. Consequently, laser pulse duration for hair removal treatments is limited in order to prevent undesirable excessive heating and damage in the epidermal layer. Techniques which provide skin surface cooling during laser treatment are able to partially mitigate the undesirable epidermal heating.

In practice, the ideal patient for laser hair removal has dark hair and fair, untanned skin. Such patients are usually best treated with high fluences (>39 J/cm$^2$) and almost always achieve reduction of hair to a sparse amount in 3-6 treatments, with minimal or no side effects. Darker skin types with dark hair have a higher incidence of side effects such as epidermal damage. To limit epidermal damage in dark skin types, treatment fluence below 40 J/cm$^2$ is often used, which also reduces efficacy and requires a higher number of treatments.

The following example is a demonstration of the invention using porcine skin to validate the effects of the device on hair removal.

Design of Individual Microneedle Fiber Tapers.

Light guiding microneedles are manufactured from large-core multimode silica fibers. These optical fibers are drawn into a tapered (needle-like) shape. The geometry in this example (~2 mm length, 40 μm average diameter, submicron tip) is based on the ~2 mm depth of human and porcine hair follicles as well as the painless microneedle design demonstrated by the mosquito. See, Meyer, W., R. Schwarz, and K. Neurand, "The skin of domestic mammals as a model for the human skin, with special reference to the domestic pig," Curr Probl Dermatol, 1978, 7: p. 39-52, the disclosure of which is incorporated by reference herein in its entirety.

Free-Space Laser Beam is Coupled into Fiber Bundle.

To effectively couple light from a free-space source, such as a laser, into the fiber microneedles, multimode fibers (MMF) with a large core diameter and high numerical aperture can be used. MMF with a core diameter of 125 μm, a cladding diameter of 140 μm, and a large numerical aperture of 0.37 are commercially available. Such fibers can be packed together tightly into a simple fiber bundle, and the end of the fiber bundle is polished flat. A simple 2-element relay lens system takes the free-space collimated beam from the laser source and focuses it into the fiber bundle with more than 50% efficiency. The maximum fluence transmitted within each needle is about ~100 kJ/cm$^2$, and is well within safe limits for standard silica optical fibers. See, Yamaguchi, S., et al., "Efficient Nd:YAG laser end pumped by a high-power multistripe laser-diode bar with multiprism array coupling.," Applied Optics, 1996, 35(9): p. 1430-1435, the disclosure of which is incorporated by reference herein in its entirety.

Light Delivery Performance in Tissue Phantoms.

Tissue-representative gelatin phantoms with dimensions ~2×10×10 mm$^3$ can be used to optimize light delivery. The scattering coefficient of the phantoms can be adjusted to mimic that of human tissues by adding IntraLipid solution (similar to dairy milk) to the gelatin solution before curing. Individual fiber microneedles are inserted into the thin side of the phantom to couple red (650 nm) light from a CW diode laser source into the fibers and capture the light scattering pattern within the phantom using a stereo microscope and CCD camera. A microneedle is optimized by quantifying the leakage length and the spatial distribution of optical fluence in turbid phantoms directly from the recorded 2D images and using these data to guide the redesign process.

Measuring the Light Delivery Performance of FMD in Tissue Phantoms and Ex Vivo Porcine Skin Using Thermal Imaging During Laser Irradiation.

The performance of the FMD using quantitative thermal imaging during light delivery can be measured with 5 W 1064 nm continuous wave laser source. Temperature images of 2×3 cm$^2$ ex vivo porcine skin specimens are measured with 100 μm spatial resolution and 16 ms temporal resolution (FLIR Thermovision A40M). The FMD can be applied to the epidermal surface of the specimens, light delivery proceeds for 2-10 s, and the thermal camera records the temperature elevation of the subdermal surface. By varying the tissue specimen thickness and microneedle insertion depth, the skin temperature profile can be mathematically reconstructed in three dimensional space and time to verify performance of the FMD.

FMD Vs. Conventional Laser Hair Removal Treatment Using Histological Analysis and Hair Counting of In Vivo Porcine Model.

Typically, a total of nine farm pigs with pigmented skin, approximately 25 kg in weight, are used. Three animals are assigned to each group, with group one evaluated one week after treatment, group two evaluated one month after treatment, and group three evaluated three months after treatment. Animals are anesthetized using 2% isofluorane gas for tattooing and laser application. On each lateral side of the dorsum, 2 cm lateral to the spine, areas 1 cm in diameter are marked to denote location for hair removal analysis. Each side of the dorsum is used experimentally to obtain duplicate measurements for each animal. High resolution photographs of the areas are taken for counting the number of hairs initially. Animals are tattooed to permanently mark treatment sites, and the skin heals for two weeks prior to light treatment application. Nine areas for evaluation of hair removal along the dorsum, parallel to the spine, allow for 2 cm spaces between each treated area.

FMD results can be compared with a conventional laser procedure which uses surface cooling to protect the epidermis. The experimental parameters to evaluate are radiative dose, and pulse duration. A Candela GentleYAG laser can be used at 1064 nm, 8-40 J/cm$^2$. Three pulse times for light application can be used: 3, 10, and 20 ms. Light is applied once for each experimental configuration. The skin is evaluated at three ending time points for number of hairs per area, and appearance of epidermal damage. At the ending time points, animals are euthanized by injection of a lethal dose of pentobarbital. Photographs of each treatment area are taken, and the treatment areas are excised and prepared for histological evaluation. Skin is sectioned, stained, and observed by light microscopy for the number of hairs in an area, any necrotic areas of tissue, or any other abnormal dermal features. Areas treated with conventional light application can be compared to areas treated with the FMD statistically by number of hairs per area.

Typically, hair removal effectiveness is substantially improved using the FMD-assisted laser procedure as compared to the conventional procedure without the FMD. The margin of improvement with FMD is greatest for higher radiative doses and longer pulse durations, where treatment effectiveness is known to be poor in pigmented tissue.

Because the devices according to embodiments of the invention can be manufactured for low cost (typically under $10), and because the needles penetrate skin, it is preferred that the device be discarded after a single-patient treatment. By improving treatment efficacy, reduction in number of treatment sessions can be achieved, saving time for patients and clinicians, and lowering the total price of healthcare. By providing a source of treatment-derived revenue (disposable FMD) the laser manufactures can also benefit.

Figure 15:
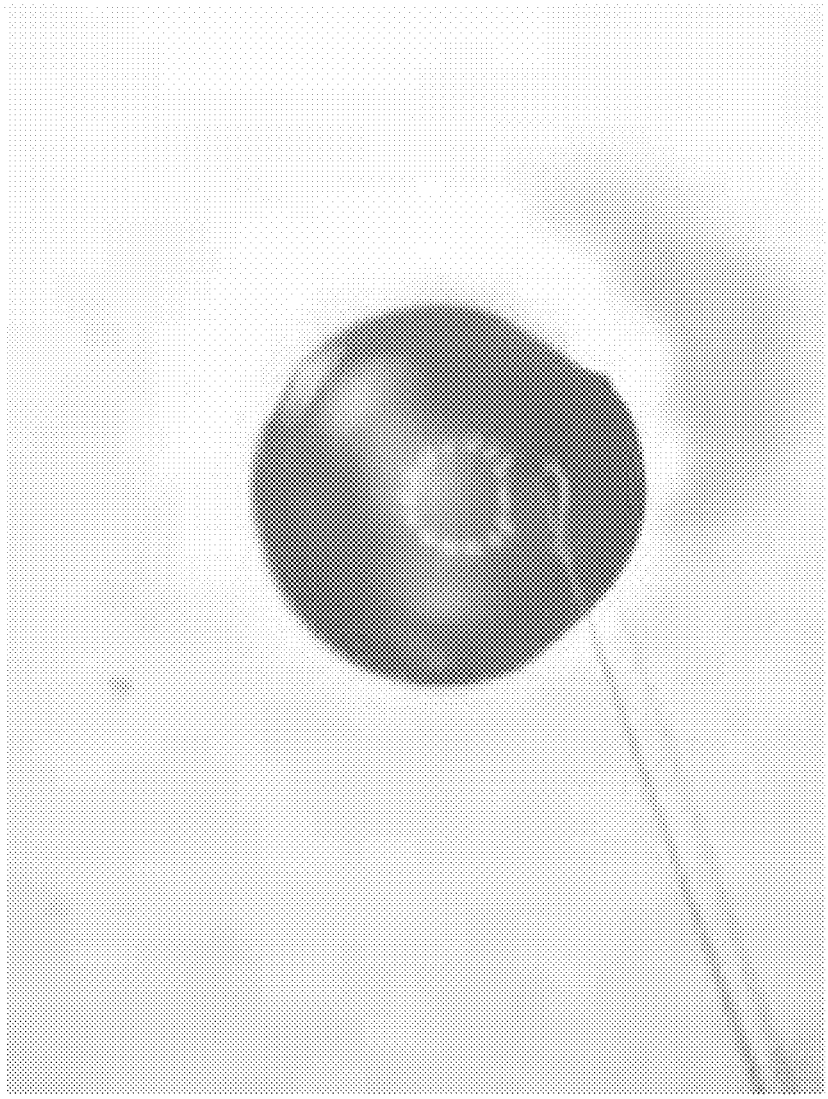
FIG. 15 is a photographic image demonstrating delivery of fluid by way of a microneedle according to the invention.

Needles of the present invention can be used for applications not requiring transmission of light and thus need not be prepared from fiberoptic material. For example, whether or not the microneedles are constructed of a material capable of transmitting light (such as silica), the microneedles can be used to deliver fluids and/or particulate matter into tissue. FIG. 15 demonstrates that embodiments of the invention can include hollow microneedles capable of permitting delivery of small volumes of fluid and particulates into tissue. Needles capable of delivering combinations of light, fluids, and/or particles are also feasible and within embodiments of the present invention. More particularly, FIG. 15 shows water delivery through a hollow silica fiber microneedle. The Fiber tip (about 20 micron outer diameter and about 10 micron inner (hole) diameter) was prepared by tapering a hollow-core silica fiber (125 micron outer diameter, 104 micron inner diameter) using a propane torch technique. Pressurized $CO_2$ (840 psi) forced water through the needle.

Figure 16:
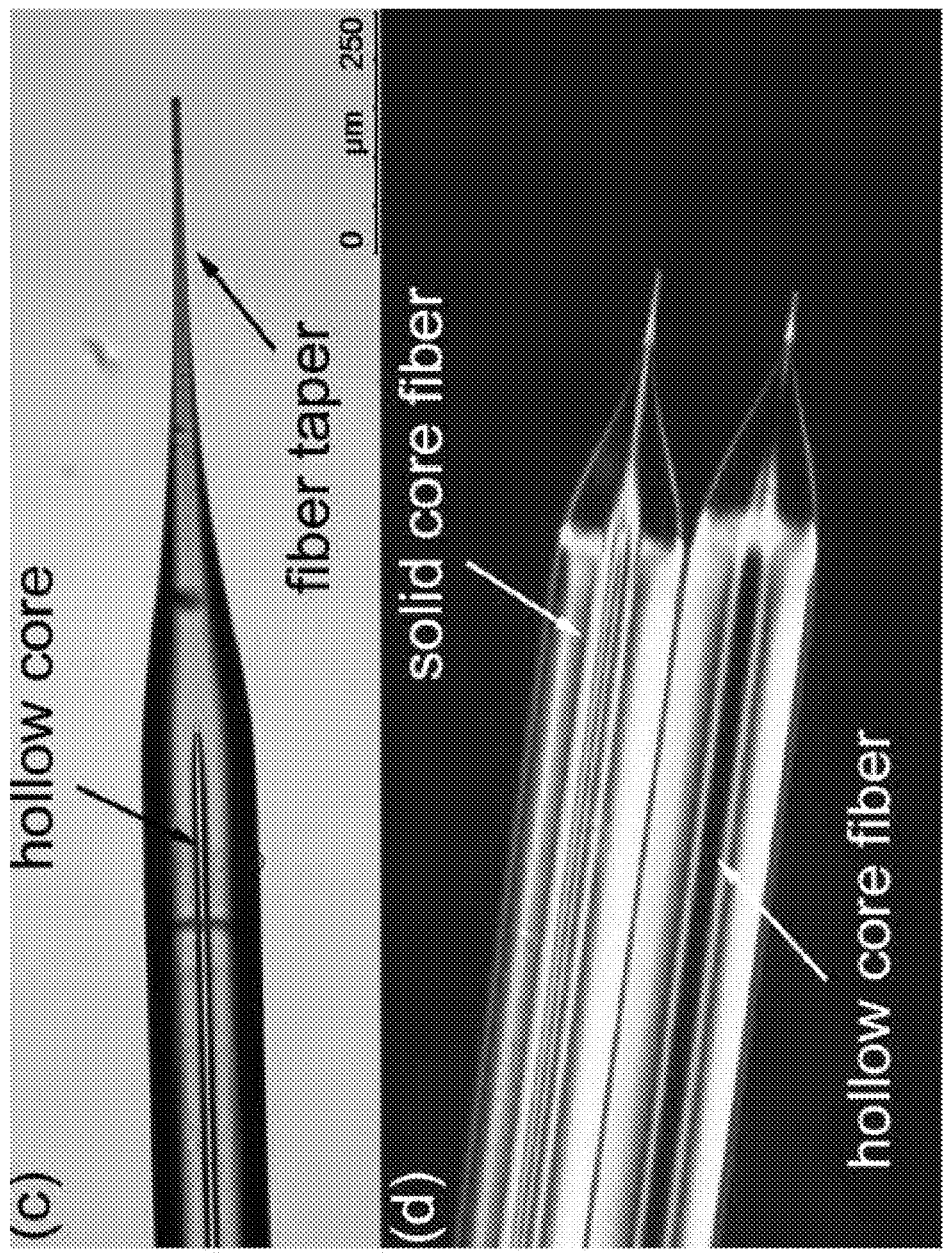
FIGS. 16C and D are optical microscope images of microneedle embodiments of the invention.
Figure 17:
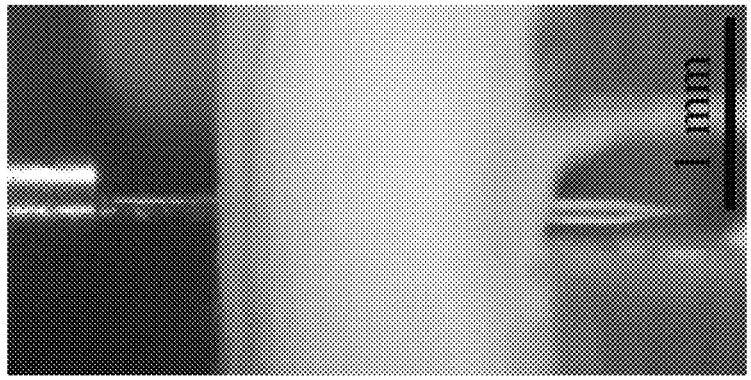
FIG. 17 is a photographic image of a microneedle penetrating skin.

Needles of embodiments of the invention can be solid core, hollow core, or even liquid core. Core and cladding materials, as well as diameters, are chosen for their ability to propagate light through the needle according to a desired application. Various needles can be combined to achieve a desired effect, for example, combining (by fusion or other means) solid core needles with hollow core needles, which are capable of transmitting light at different rates and/or wavelengths (e.g., single mode and multi-mode fibers can be combined). FIG. 16 shows optical microscope images of a hollow core fiber taper (top) and the combination of a hollow core fiber taper fused with a solid core fiber taper (bottom).

The needles, systems, and methods of embodiments of the invention can be adapted for use with any laser-based treatment or diagnostic in which light is used to detect or treat targets under or on the skin surface. Targets include, but are not limited to, blood vessels (e.g., treatment of varicose veins), skin (e.g., skin reshaping), hair follicles (e.g., unwanted hair removal), subdermal fat (e.g., liposuction and fat reshaping), tattoo particles (e.g., tattoo removal), and port wine stain removal. Indeed any treatment including oncology treatments, dermatology treatments, cosmetic surgeries and procedures, alternative medicine protocols (e.g., acupuncture), treatment of bladder cancer, and treatment of deep skin cancers (e.g., by way of minimally invasive laser-based hyperthermia therapy of cancers under the skin, such as melanoma) can be improved by reducing patient pain and/or recovery time and skin damage.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

The invention claimed is:

1. A needle device comprising:
    (a) an optical fiber needle with:
    (i) a cylindrical optical fiber shaft extending from a base to a tip, wherein the optical fiber shaft is operably configured for guiding light;
    (ii) a base with a maximum outer diameter of about 50 µm to 500 µm;
    (iii) a tip having an outer diameter smaller than the outer diameter of the base, wherein the tip has an end operably configured for piercing human tissue; and
        (b) one or more compressible ferrules, wherein the optical fiber needle tip end is disposed within a support when the compressible ferrule is in an uncompressed state.

2. The needle device of claim 1, wherein the needle does not comprise metal.

3. The needle device of claim 1, wherein the optical fiber shaft is solid.

4. The needle device of claim 1, wherein the optical fiber shaft is hollow and is shaped and sized to allow for fluids or particles to pass through the optical fiber shaft.

5. The needle device of claim 4, wherein the hollow optical fiber shaft is operably configured for co-localized or simultaneous light and fluid delivery.

6. The needle device of claim 1 comprising a tip end that is sharp, sharpened, tapered, angled, polished, or beveled.

7. The needle device of claim 1, wherein the optical fiber shaft has a base with an outer diameter in the range of about 200-500 µm.

8. The needle device of claim 1, wherein the optical fiber shaft has a tip with an outer diameter ranging from a submicron diameter up to 10% of the outer diameter of the base.

9. The needle device of claim 1, wherein the optical fiber shaft is silica.

10. The needle device of claim 9, wherein the optical fiber shaft comprises multi-mode silica fiber.

11. The needle device of claim 1, wherein the optical fiber shaft comprises a light-blocking coating.

12. The needle device of claim 1 comprising a light source operably connected with the needle to transmit light through the optical fiber shaft.

13. The needle device of claim 1, wherein the optical fiber needle base has a maximum outer diameter of 50 µm to under 200 µm.

14. A fiberoptic microneedle device comprising:
    (a) one or more needles comprising:
    (i) a cylindrical optical fiber shaft extending from a base to a tip, wherein the optical fiber shaft is operably configured for guiding light;
    (ii) a base with a maximum outer diameter of about 50 µm to 500 µm; and
    (iii) a tip having an outer diameter smaller than the outer diameter of the base, wherein the tip has an end operably configured for piercing human tissue; and
        (b) one or more ferrules comprising a compressible material for causing retraction of the tip ends into a support when the ferrule is in an uncompressed state.

15. The device of claim 14 comprising an array of needles.

16. The device of claim 14, further comprising one or more ferrules of a non-compressible material.

17. The device of claim 14 comprising an electrical, mechanical, pneumatic, or hydraulic actuation source for inserting, moving, or causing protrusion of the one or more needles into, within, or from the one or more ferrules.

18. The device of claim 14 operably configured for applying positive or negative vacuum pressure for temporarily securing one or more of the ferrules to a surface and stabilizing the device for insertion of one or more of the needles into the surface from and through the one or more ferrules.

19. The device of claim 14 further comprising a control system with feedback capabilities to monitor and control one or more of power or duration of light delivery from one or more of the needles; pressure, volume, or rate of flow of fluids or particles through one or more of the needles; or depth of protrusion of one or more of the needles from the ferrules.

20. The device of claim 19, wherein the control system is operably configured to monitor and control delivery and removal of fluids through one or more of the needles.

21. The device of claim 19, wherein the optical fiber shaft is hollow and is operably configured for co-localized or simultaneous light and fluid delivery.

22. A method of performing photothermal, photochemical, or photomechanical therapy in tissue or of detecting disease in tissue comprising:

placing the needle device of claim 1 in contact with a surface of tissue;

compressing one or more of the compressible ferrules such that the needle tip end protracts from the support and penetrates the tissue surface;

delivering light on, in, or below the tissue surface such that photothermal, photochemical, or photomechanical therapy is administered to one or more of cancer, blood vessels, hair follicles, subdermal fat, tattoo particles, or skin.

23. A method of performing photothermal, photochemical, or photomechanical therapy in tissue or of detecting disease in tissue comprising:

placing the fiberoptic microneedle device of claim 14 in contact with tissue;

compressing one or more of the compressible ferrules such that upon compression the tip ends of the needles penetrate a surface of the tissue; and delivering light on, in, or below the tissue surface using the fiberoptic microneedle device such that photothermal, photochemical, or photomechanical therapy is administered to one or more of cancer, blood vessels, hair follicles, subdermal fat, tattoo particles, or skin.

* * * * *